US012691114B2

(12) United States Patent
Boger

(10) Patent No.: US 12,691,114 B2
(45) Date of Patent: Jul. 28, 2026

(54) COMPOSITIONS FOR INHIBITION OF HERPESVIRUSES

(71) Applicant: The Medical College of Wisconsin, Inc., Milwaukee, WI (US)

(72) Inventor: Ravit Boger, Baltimore, MD (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 887 days.

(21) Appl. No.: 17/794,820

(22) PCT Filed: Jan. 22, 2021

(86) PCT No.: PCT/US2021/014764
§ 371 (c)(1),
(2) Date: Jul. 22, 2022

(87) PCT Pub. No.: WO2021/150998
PCT Pub. Date: Jul. 29, 2021

(65) Prior Publication Data

US 2023/0097057 A1 Mar. 30, 2023

Related U.S. Application Data

(60) Provisional application No. 62/965,755, filed on Jan. 24, 2020.

(51) Int. Cl.

| | |
|---|---|
| ***A61K 31/4985*** | (2006.01) |
| ***A61K 31/341*** | (2006.01) |
| ***A61K 31/407*** | (2006.01) |
| ***A61K 31/454*** | (2006.01) |
| ***A61K 31/475*** | (2006.01) |

(Continued)

(52) U.S. Cl.
CPC ........ *A61K 31/4985* (2013.01); *A61K 31/341* (2013.01); *A61K 31/407* (2013.01); *A61K 31/454* (2013.01); *A61K 31/475* (2013.01); *A61K 31/496* (2013.01);
(Continued)

(58) Field of Classification Search
CPC .............. A61K 2300/00; A61K 31/341; A61K 31/407; A61K 31/454; A61K 31/4725; A61K 31/475; A61K 31/496; A61K 31/4985; A61K 31/4995; A61K 31/517; A61K 31/522; A61K 45/06; A61P 31/22;
(Continued)

(56) References Cited

U.S. PATENT DOCUMENTS

| | | | |
|---|---|---|---|
| 10,556,894 | B2 | 2/2020 | Remiszewski et al. |
| 11,358,961 | B2 | 6/2022 | Remiszewski et al. |

(Continued)

FOREIGN PATENT DOCUMENTS

| | | | |
|---|---|---|---|
| WO | 2004/111049 | A1 | 12/2004 |
| WO | 2016077232 | A2 | 5/2016 |
| WO | 2019152808 | A1 | 8/2019 |

OTHER PUBLICATIONS

Fader, Lee et al., "Discovery of Potent, Orally Bioavailable Inhibitors of Human Cytomegalovirus", ACS Med. Chem. Lett. 2016, 7, 525-530.

(Continued)

*Primary Examiner* — Savitha M Rao
(74) *Attorney, Agent, or Firm* — Quarles & Brady LLP

(57) ABSTRACT

The disclosure herein provides compounds of formulas I-V which are useful in the inhibition of viral diseases in a subject. In some embodiments, the compounds of formulas I-V are useful in the inhibition of herpes viruses.

6 Claims, 11 Drawing Sheets

Specification includes a Sequence Listing.

(51) Int. Cl.
*A61K 31/496* (2006.01)
*A61K 31/517* (2006.01)
*A61K 31/522* (2006.01)
*A61P 31/22* (2006.01)

(52) U.S. Cl.
CPC .......... *A61K 31/517* (2013.01); *A61K 31/522* (2013.01); *A61P 31/22* (2018.01)

(58) Field of Classification Search
CPC .. C07D 307/68; C07D 401/12; C07D 487/04; C07D 495/04; C07D 513/04
See application file for complete search history.

(56) References Cited

U.S. PATENT DOCUMENTS

| | | | |
|---|---|---|---|
| 2009/0163545 A1 | 6/2009 | Goldfarb |
| 2010/0152200 A1 | 6/2010 | Miller et al. |
| 2017/0216285 A1 | 8/2017 | Leaner et al. |
| 2018/0291016 A1 | 10/2018 | Remiszewski et al. |
| 2020/0140429 A1 | 5/2020 | Remiszewski et al. |
| 2021/0137960 A1 | 5/2021 | Hansen et al. |
| 2022/0135556 A1 | 5/2022 | Remiszewski et al. |

OTHER PUBLICATIONS

Pharmaceutics and Pharmacy Practice, J.B. Lippincott Company, Philadelphia, PA, Banker and Chalmers, eds., pp. 238-250 (1982).
ASHP Handbook on Injectable Drugs, Trissel, 15th ed., pp. 622-630 (2009).
Staras, S. A; Dollard, S. C .; Radford, K. W.; Flanders, W. D.; Pass, R. F.; Cannon, M. J. Seroprevalence of cytomegalovirus infection in the United States, 1988-1994. Clin. Infect. Dis 2006, 43, 1143-1151.
Griffiths, P. D.; Clark, D. A; Emery, V. C. Betaherpesviruses in transplant recipients. J Antimicrob. Chemother 2000, 45 Suppl T3, 29-34.
Kovacs, A; Schluchter, M.; Easley, K.; Demmler, G.; Shearer, W.; La, R. P.; Pitt, J.; Cooper, E.; Goldfarb, J.; Hodes, D.; Kattan, M.; McIntosh, K. Cytomegalovirus infection and HIV-I disease progression in infants born to HIV-I-infected women. Pediatric Pulmonary and Cardiovascular Complications of Vertically Transmitted HIV Infection Study Group. N Engl. J Med 1999, 341, 77-84.
Sabin, C. A; Phillips, AN.; Lee, C. A; Janossy, G.; Emery, V.; Griffiths, P. D. The effect of CMV infection on progression of human immunodeficiency virus disease is a cohort of haemophilic men followed for up to 13 years from seroconversion. Epidemiol Infect 1995, 114, 361-72.
Sabin, C. A; Devereux, H. L.; Clewley, G.; Emery, V. C.; Phillips, AN.; Loveday, C.; Lee, C. A; Griffiths, P. D. Cytomegalovirus seropositivity and human immunodeficiency virus type I RNA levels in individuals with hemophilia. J Infect Dis 2000, 181, 1800-3.
Demmler, G. J. Infectious Diseases Society of America and Centers for Disease Control. Summary of a workshop on surveillance for congenital cytomegalovirus disease. Rev. Infect. Dis 1991, 13, 315-329.
Boeckh, M.; Nichols, W. G.; Papanicolaou, G.; Rubin, R.; Wingard, J. R.; Zaia, J. Cytomegalovirus in hematopoietic stem cell transplant recipients: Current status, known challenges, and future strategies. Biol. Blood Marrow Transplant 2003, 9, 543-558.
Boivin, G.; Goyette, N.; Rollag, H.; Jardine, AG.; Pescovitz, M. D.; Asberg, A; Ives, J.; Hartmann, A; Humar, A Cytomegalovirus resistance in solid organ transplant recipients treated with intravenous ganciclovir or oral valganciclovir. Antivir. Ther 2009, 14, 697-704.
Kimberlin, D. W.; Lin, C. Y.; Sanchez, P. J.; Demmler, G. J.; Dankner, W.; Shelton, M.; Jacobs, R. F.; Vaudry, W.; Pass, R. F.; Kiell, J.M.; Soong, S. J.; Whitley, R. J. Effect of ganciclovir therapy on hearing in symptomatic congenital cytomegalovirus disease involving the central nervous system: a randomized, controlled trial. J Pediatr 2003, 143, 16-25.
Schreiber, A; Harter, G.; Schubert, A; Bunjes, D.; Mertens, T.; Michel, D. Antiviral treatment of cytomegalovirus infection and resistant strains. Expert. Opin. Pharmacother 2009, 10, 191-209.
Steininger, C. Novel therapies for cytomegalovirus disease. Recent Pat Antiinfect. Drug Discov 2007, 2, 53-72.
Chou, S. W. Cytomegalovirus drug resistance and clinical implications. Transpl. Infect. Dis 2001, 3 Suppl 2, 20-24.
Avery, R. K.; Arav-Boger, R.; Marr, K. A; Kraus, E.; Shoham, S.; Lees, L.; Trollinger, B.; Shah, P.; Ambinder, R.; Neofytos, D.; Ostrander, D.; Forman, M.; Valsamakis, A Outcomes in Transplant Recipients Treated with Foscamet for Ganciclovir-Resistant or Refractory Cytomegalovirus Infection. Transplantation 2016.
Kimberlin, D. W.; et al. Valganciclovir for symptomatic congenital cytomegalovirus disease. N Engl. J Med 2015, 372, 933-943.
Chou, S.; Ercolani, R. J.; Lanier, E. R. Novel Cytomegalovirus UL54 DNA Polymerase Gene Mutations Selected In Vitro That Confer Brincidofovir Resistance. Antimicrob Agents Chemother 2016, 60, 3845-8.
Chou, S. Rapid In Vitro Evolution of Human Cytomegalovirus UL56 Mutations That Confer Letermovir Resistance. Antimicrob Agents Chemother 2015, 59, 6588-93.
Chemaly, R. F.; Ullmann, A J.; Stoelben, S.; Richard, M. P.; Bomhauser, M.; Groth, C.; Einsele, H.; Silverman, M.; Mullane, K. M.; Brown, J.; Nowak, H.; Kolling, K.; Stobemack, H.P.; Lischka, P.; Zimmermann, H.; Rubsamen-Schaeff, H.; Champlin, R. E.; Ehninger, G. Letermovir for cytomegalovirus prophylaxis in hematopoietic-cell transplantation. N Engl. J Med 2014, 370, 1781-1789.
Frietsch, J. J.; Michel, D.; Stamminger, T.; Hunstig, F.; Birndt, S.; Schnetzke, U.; Scholl, S.; Hochhaus, A; Hilgendorf, I. In Vivo Emergence ofUL56 C325Y Cytomegalovirus Resistance to Letermovir in a Patient with Acute Myeloid Leukemia after Hematopoietic Cell Transplantation. Mediterr J Hematol Infect Dis 2019, 11, e2019001.
Papanicolaou, G. A; Silveira, F. P.; Langston, A A; Pereira, M. R.; Avery, R. K.; Uknis, M.; Wijatyk, A; Wu, J.; Boeckh, M.; Marty, F. M.; Villano, S. Maribavir forRefractory or Resistant Cytomegalovirus Infections in Hematopoietic-cell or Solid-organ Transplant Recipients: A Randomized, Dose-ranging, Double-blind, Phase 2 Study. Clin Infect Dis 2018, 68, 1255-1264.
He, R.; Sandford, G.; Hayward, G. S.; Burns, W. H.; Posner, G. H.; Forman, M.; Ara••Boger, R. Recombinant luciferase-expressing human cytomegalovirus (CMV) for evaluation of CMV inhibitors. Viral. J20II, 8, 40.
Inglese, J.; Auld, D. S.; Jadhav, A; Johnson, R. L.; Simeonov, A; Yasgar, A; Zheng, W.; Austin, C. P. Quantitative high-throughput screening: a titration-based approach that efficiently identifies biological activities in large chemical libraries. Proc Natl Acad Sci US A 2006, 103, 11473-8.
Shen, L.; Peterson, S.; Sedaghat, AR.; McMahon, M. A; Callender, M.; Zhang, H.; Zhou, Y.; Pitt, E.; Anderson, K. S.; Acosta, E. P.; Siliciano, R. F. Dose-response curve slope sets class-specific limits on inhibitory potential of anti-HIV drugs. Nat. Med 2008, 14, 762-766.
Sampah, M. E.; Shen, L.; Jilek, B. L.; Siliciano, R. F. Dose-response curve slope is a missing dimension in the analysis of HIV-I drug resistance. Proc. Natl. Acad Sci. U S. A 2011, 108, 7613-7618.
Jacobson, J. G.; Renau, T. E.; Nassiri, M. R.; Sweier, D. G.; Breitenbach, J. M.; Townsend, L.B.; Drach, J.C. Nonnucleoside pyrrolopyrimidines with a unique mechanism of action against human cytomegalovirus. Antimicrob. Agents Chemother 1999, 43, 1888-1894.
Straschewski, S.; Warmer, M.; Frascaroli, G.; Hohenberg, H.; Mertens, T.; Winkler, M. Human cytomegaloviruses expressing yellow fluorescent fusion proteins—characterization and use in antiviral screening. PLoS. One 2010, 5, e9174.
Gilbert, C.; Boivin, G. New reporter cell line to evaluate the sequential emergence of multiple human cytomegalovirus mutations during in vitro drug exposure. Antimicrob. Agents Chemother 2005, 49, 4860-4866.

(56) References Cited

OTHER PUBLICATIONS

Fukui, Y.; Shindoh, K.; Yamamoto, Y.; Koyano, S.; Kosugi, I.; Yamaguchi, T.; Kurane, I.; Inoue, N. Establishment of a cell-based assay for screening of compounds inhibiting very early events in the cytomegalovirus replication cycle and characterization of a compound identified using the assay. Antimicrob. Agents Chemother 2008, 52, 2420-2427.

Beelontally, R.; Wilkie, G. S.; Lau, B.; Goodmaker, C. J.; Ho, C. M.; Swanson, C. M.; Deng, X.; Wang, J.; Gray, N. S.; Davison, A J.; Strang, B. L. Identification of compounds with anti-human cytomegalovirus activity that inhibit production of IE2 proteins. Antiviral Res 2017, 138, 61-67.

Mercorelli, B.; Palu, G.; Loregian, A Drug Repurposing for Viral Infectious Diseases: How Far Are We? Trends Microbiol 2018, 26, 865-876.

Mercorelli, B.; Luganini, A; Nannetti, G.; Tabarrini, O.; Palu, G.; Gribaudo, G.; Loregian, A Drug Repurposing Approach Identifies Inhibitors of the Prototypic Viral Transcription Factor IE2 that Block Human Cytomegalovirus Replication. Cell Chem Biol 2016, 23, 340-51.

Gardner, T. J.; Cohen, T.; Redmann, V.; Lau, Z.; Felsenfeld, D.; Tortorella, D. Development of a high-content screen for the identification of inhibitors directed against the early steps of the cytomegalovirus infectious cycle. Antiviral Res 2015, 113, 49-61.

Nukui, M.; O'Connor, C. M.; Murphy, E. A The Natural Flavonoid Compound Deguelin Inhibits HCMV Lytic Replication within Fibroblasts. Viruses 2018, 10, 614.

Lischka, P.; Hewlett, G.; Wunberg, T.; Baumeister, J.; Paulsen, D.; Goldner, T.; Ruebsamen-Schaeff, H.; Zimmermann, H. In vitro and in vivo activities of the novel anticytomegalovirus compound AIC246. Antimicrob. Agents Chemother 2010, 54, 1290-1297.

Goldner, T.; Hewlett, G.; Ettischer, N.; Ruebsamen-Schaeff, H.; Zimmermann, H.; Lischka, P. The novel anticytomegalovirus compound AIC246 (Letermovir) inhibits human cytomegalovirus replication through a specific antiviral mechanism that involves the viral terminase. J Virol 201 I, 85, 10884-93.

Perez, M.; Lamothe, M.; Maraval, C.; Mirabel, E.; Loubat, C.; Planty, B.; Horn, C.; Michaux, J.; Marrot, S.; Letienne, R.; Pignier, C.; Bocquet, A; Nadal-Wollbold, F.; Cussac, D.; de Vries, L.; Le Grand, B. Discovery of novel protease activated receptors 1 antagonists with potent antithrombotic activity in vivo. J Med Chem 2009, 52, 5826-36.

Srinivasan, S.; Schuster, G. B. A conjoined thienopyrrole oligomer formed by using DNA as a molecular guide. Org Lett 2008, 10, 3657-60.

Kapoor, A; Cai, H.; Forman, M.; He, R.; Shamay, M.; Arav-Boger, R. Human cytomegalovirus inhibition by cardiac glycosides: evidence for involvement of the HERG gene. Antimicrob. Agents Chemother 2012, 56, 4891-4899.

Li, R.; Zhu, J.; Xie, Z.; Liao, G.; Liu, J.; Chen, M. R.; Hu, S.; Woodard, C.; Lin, J.; Taverna, S. D.; Desai, P.; Ambinder, R. F.; Hayward, G. S.; Qian, J.; Zhu, H.; Hayward, S. D. Conserved Herpesvirus Kinases Target the DNA Damage Response Pathway and TIP60 Histone Acetyltransferase to Promote Virus Replication. Cell Host. Microbe 2011, 10, 390-400.

Forman, M. S.; Vaidya, D.; Bolorunduro, O.; Diener-West, M.; Pass, R. F.; Ara •• Boger, R. Cytomegalovirus Kinetics Following Primary Infection in Healthy Women. J Infect Dis 2017, 215, 1523-1526.

Cai, H.; Kapoor, A; He, R.; Venkatadri, R.; Forman, M.; Posner, G. H.; Arav-Boger, R. In Vitro Combination of Anti-Cytomegalovirus Compounds Acting through Different Targets: Role of the Slope Parameter and Insights into Mechanisms of Action. Antimicrob. Agents Chemother 2014, 58, 986-994.

Jilek, B. L.; Zarr, M.; Sampah, M. E.; Rabi, S. A; Bullen, C. K.; Lai, J.; Shen, L.; Siliciano, R. F. A quantitative basis for antiretroviral therapy for HIV-I infection. Nat. Med 2012, 18, 446-451.

Van der Watt, P. et al., Targeting the Nuclear Import Receptor KpnB1 as an Anticancer Therapeutic, Mol. Cancer Ther; 15(4), Apr. 2016, 560-573.

Kapoor, A. et al., Validation and Characterization of Five Distinct Novel Inhibitors of Human Cytomegalovirus, Journal of Medicinal Chemistry, 2020, 63(8):3896-3907.

NIH—National Library of Medicine, PubChem CID 1275864, Jul. 10, 2005, 11 pages.

NIH—National Library of Medicine, PubChem CID 2021006, Jul. 13, 2005, 10 pages.

NIH—National Library of Medicine, PubChem CID 16018446, Apr. 2, 2007, 10 pages.

NIH—National Library of Medicine, PubChem CID 16403899, Jul. 30, 2007, 10 pages.

NIH—National Library of Medicine, PubChem SID 289747550, Jan. 18, 2016, 5 pages.

PCT International Search Report and Written Opinion, PCT/US2021/014764, Apr. 16, 2021, 18 pages.

European Patent Office, Extended Search Report, Application No. 21744968.5, Apr. 15, 2024, 13 pages.

| No. | Chemical Name | Structure | Molecular weight |
|---|---|---|---|
| 1 | MLS000108969 ($C_{19}H_{15}ClN_2O_4$) |  | 370.80 |
| 2 | NCGC00121827 ($C_{26}H_{31}N_5O_2S$) |  | 477.63 |
| 3 | MLS001158554 ($C_{29}H_{30}N_4O_2$) |  | 466.57 |
| 4 | MLS000558091 ($C_{21}H_{16}N_4O_2S_2$) |  | 420.51 |
| 5 | NCGC00112955 ($C_{23}H_{26}ClN_3O_2S$) |  | 443.99 |

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Primer forward 5

<400> SEQUENCE: 1

gcgtgctttt tagcctctgc a                                               21


<210> SEQ ID NO 2
<211> LENGTH: 22
<212> TYPE: DNA
<213> ORGANISM: Artificial Sequence
<220> FEATURE:
<223> OTHER INFORMATION: Primer reverse 5

<400> SEQUENCE: 2
```

-continued aaaagtttgt gccccaacgg ta 22

<210> SEQ ID NO 3
<211> LENGTH: 22
<212> TYPE: DNA
<213> ORGANISM: Artificial Sequence
<220> FEATURE:
<223> OTHER INFORMATION: US17 probe FAM 5'

<400> SEQUENCE: 3
tgatcgggcg ttatcgcgtt ct 22

COMPOSITIONS FOR INHIBITION OF HERPESVIRUSES

CROSS-REFERENCE TO RELATED APPLICATIONS

This application is the U.S. National Phase entry of PCT International Application No. PCT/US2021/014764 Jan. 22, 2021, which claims the benefit of U.S. Appl. No. 62/965,755, filed Jan. 24, 2020, the disclosure of which is incorporated herein by reference in its entirety.

STATEMENT OF GOVERNMENTAL INTEREST

The This invention was made with government support under grant no. 1R01DC013550 awarded by the National Institutes of Health. The government has certain rights in the invention.

SEQUENCE LISTING

This application contains a sequence listing which has been submitted electronically in ASCII format and is hereby incorporated by reference in its entirety. Said ASCII copy, created on Jan. 22, 2021, is named 2635-0001WO01_Sequence Listing_ST25.txt and is 1 KB in size.

BACKGROUND OF THE INVENTION

Infection with human cytomegalovirus (HCMV), a member of the herpesvirus family, is common in humans. Seroprevalence rates reach 90% in individuals older than 80 years[1]. While infection is usually asymptomatic, HCMV continues to be a serious threat for transplant recipients and patients with AIDS. It is also the most common congenital infection worldwide, causing hearing loss, global disabilities, and central nervous system damage in children[2-6].

The nucleoside analog ganciclovir (GCV) and its oral formulation val-GCV have dramatically improved the outcome of transplantations by reducing sequelae from HCMV replication and disease[7, 8]. GCV was also shown to prevent hearing deterioration in congenitally infected children[9]. However, prolonged courses of GCV or val-GCV result in serious toxicities to the bone marrow[10-13]. A phase III clinical trial of oral val-GCV in congenitally-infected infants concluded that 6 months' therapy may have a better neurological outcome than 6 weeks, but GCV-resistant mutants emerge[14]. Similarly, GCV-resistant mutants emerge in transplant recipientsis,[15, 16] When GCV resistance arises, the limited therapeutic alternatives, foscarnet and cidofovir, are highly nephrotoxic and can only be administered intravenously. Their use in cases of resistant or refractory HCMV is associated with high morbidity and mortality[13]. Several new drugs have advanced into FDA approval and clinical trials. The terminase inhibitor letermovir was recently approved for HCMV prophylaxis after hematopoietic bone marrow transplantation[17]. Rapid selection of UL56 mutations in cell culture[16] and letermovir resistance in patients are being reported[18]. Maribavir, a viral UL97 kinase inhibitor, is in clinical trials[19].

Identification of new herpesvirus inhibitors is an important area of drug development. Although several drugs are available there is a clear need to improve the currently available drugs, given the toxicities of available agents and the ongoing selection of drug resistant mutants.

SUMMARY OF THE INVENTION

Disclosed herein are methods of inhibiting a human herpesvirus in a subject in need thereof, comprising administering to the subject a compound of formula I or a pharmaceutical composition thereof comprising a pharmaceutically acceptable carrier (I)

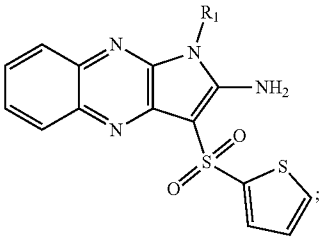

or a salt, solvate, or stereoisomer thereof, wherein $R_1$ is a cycloalkyl, heterocycloalkyl, aryl, or heteroaryl optionally substituted with one or more alkyl, amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group. In some embodiments, the compound is selected from the group consisting of:

(A)

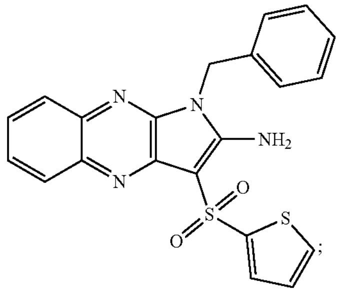

(B)

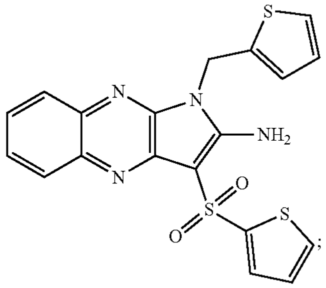

and (C)

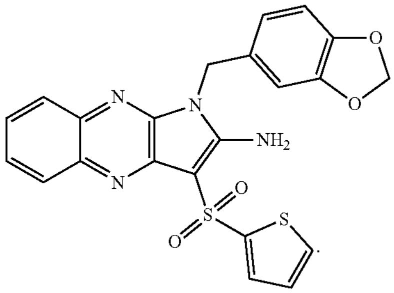

Disclosed herein are methods of inhibiting a human herpesvirus in a subject in need thereof, comprising administering to the subject a compound of formula II or a pharmaceutical composition thereof comprising a pharmaceutically acceptable carrier:

(II)

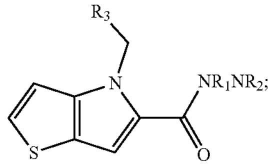

or a salt, solvate, or stereoisomer thereof, wherein $R_1$ is H, and $R_2$ is independently H or alkyl, alkenyl, alkynyl, cycloalkyl, heterocycloalkyl, aryl, or heteroaryl, optionally substituted with one or more alkyl, amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group; or $R_1$ and $R_2$ together form a $C_1$-$C_6$ heterocycloalkyl, or $C_1$-$C_6$ heteroaryl optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms; and wherein $R_3$ is H or cycloalkyl, heterocycloalkyl, aryl, or heteroaryl, optionally substituted with one or more halo, $CF_3$, CN, and $NO_2$ moieties. In some embodiments, $R_2$ is $C_1$-$C_6$ heterocycloalkyl or $C_1$-$C_6$ heteroaryl, optionally substituted with one or more alkyl, amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group. In some embodiments, the compound is selected from the group consisting of:

(D)

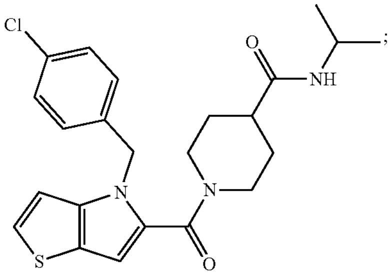

(E)

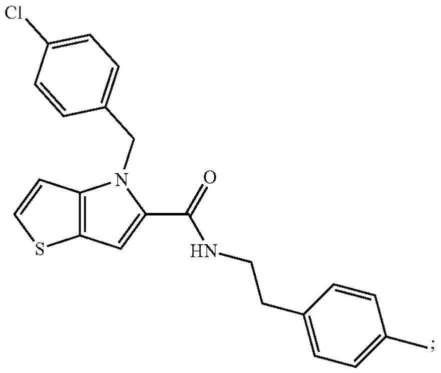

and

-continued (F)

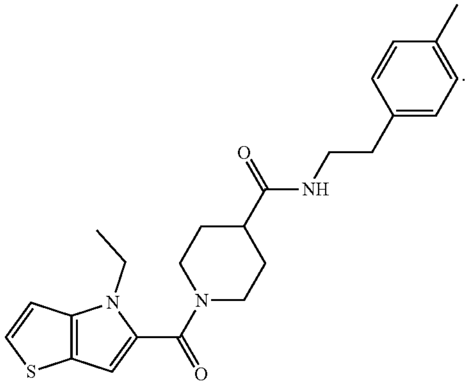

Disclosed herein are methods of inhibiting a human herpesvirus in a subject in need thereof, comprising administering to the subject a compound of formula III or a pharmaceutical composition thereof comprising a pharmaceutically acceptable carrier:

(III)

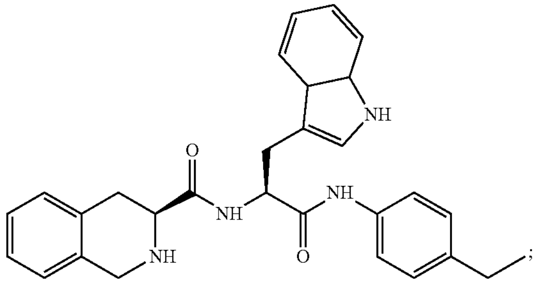

or a salt, solvate, or stereoisomer thereof.

Disclosed herein are methods of inhibiting a human herpesvirus in a subject in need thereof, comprising administering a compound of formula IV or a pharmaceutical composition thereof comprising a pharmaceutically acceptable carrier:

(IV)

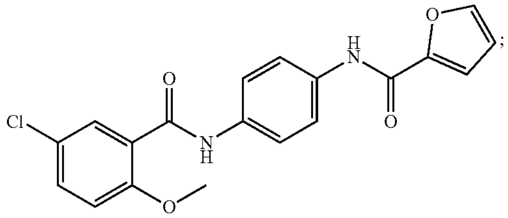

or a salt, solvate, or stereoisomer thereof.

Disclosed herein are methods of inhibiting a human herpesvirus in a subject in need thereof, comprising administering to the subject a compound of formula V or a pharmaceutical composition thereof comprising a pharmaceutically acceptable carrier:

(V)

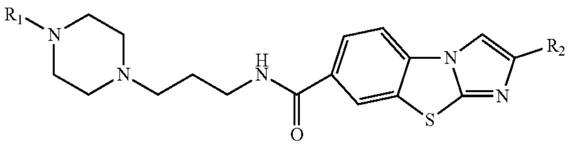

or a salt, solvate, or stereoisomer thereof, wherein $R^1$ is hydrogen, $C_1$-$C_6$ straight or branched alkyl, or $C_3$-$C_6$ cycloalkyl; and $R^2$ is phenyl, unsubstituted or substituted with $R^3$ or $OR^3$, wherein $R^3$ is hydrogen, $C_1$-$C_6$ straight or branched alkyl, or $C_3$-$C_6$ cycloalkyl. In some embodiments, $R^1$ is $C_1$-$C_4$ straight or branched alkyl; and $R^2$ is phenyl substituted with $OR^3$, wherein $R^3$ is $C_1$-$C_4$ straight or branched alkyl. In some embodiments, the compound is (G)

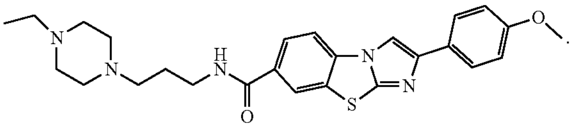

In some embodiments, the methods disclosed herein further comprise administering more than one biologically active agent, such as two, three, four, or more biologically active agents.

In some embodiments, the herpesvirus is selected from the group consisting of human herpesvirus 1 (HHV-1), human herpesvirus 2 (HHV-2), human herpesvirus 3 (HHV-3), human herpesvirus 4 (HHV-4), human herpesvirus 5 (HHV-5), human herpesvirus 6 (HHV-6), human herpesvirus 7 (HHV-7), and human herpesvirus 8 (HHV-8). In some embodiments, the herpesvirus is HHV-5.

Disclosed herein are pharmaceutical compositions comprising a compound of formula I:

(I)

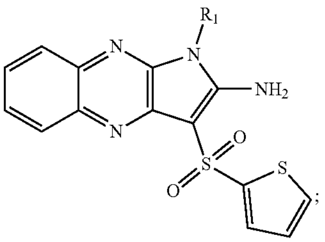

or a salt, solvate, or stereoisomer thereof, wherein $R_1$ is a cycloalkyl, heterocycloalkyl, aryl, or heteroaryl optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group, and a pharmaceutically acceptable carrier. In some embodiments, the compounds are selected from the group consisting of:

(A)

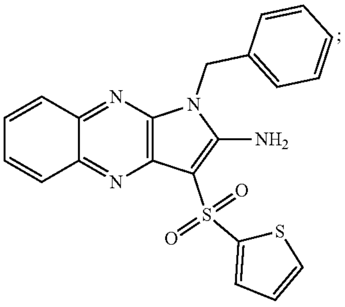

(B)

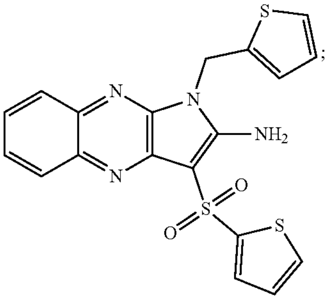

and (C)

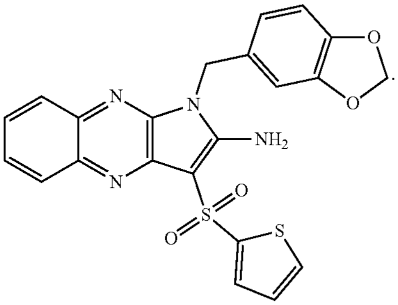

Disclosed herein are pharmaceutical compositions comprising a compound of formula II:

(II)

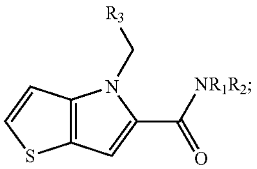

or a salt, solvate, or stereoisomer thereof, wherein $R_1$ is H, and $R_2$ is independently H or alkyl, alkenyl, alkynyl, cycloalkyl, heterocycloalkyl, aryl, or heteroaryl, optionally substituted with one or more alkyl, amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group; or $R_1$ and $R_2$ together form a $C_1$-$C_6$ heterocycloalkyl, or $C_1$-$C_6$ heteroaryl optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms; and wherein $R_3$ is H or cycloalkyl, heterocycloalkyl, aryl, or heteroaryl, optionally substituted with one or more halo, $CF_3$, CN, and $NO_2$ moieties. In some embodiments, $R_2$ is $C_1$-$C_6$ heterocycloalkyl or $C_1$-$C_6$ heteroaryl, optionally substituted with one or more alkyl, amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group. In some embodiments, the compound is selected from the group consisting of:

(D)

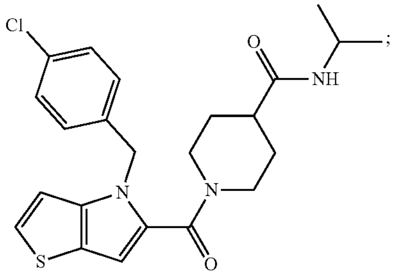

(E)

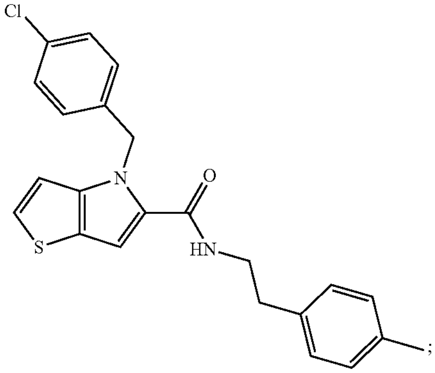

and (F)

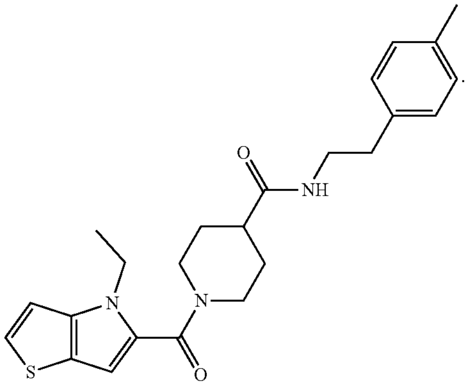

Disclosed herein are pharmaceutical compositions comprising a compound of formula III:

(III)

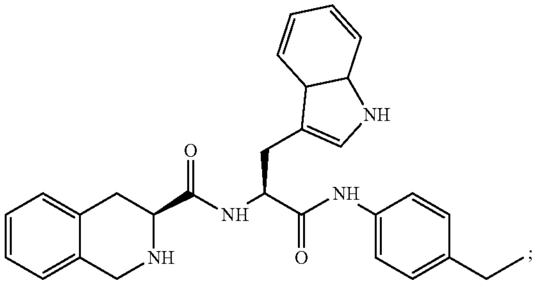

or a salt, solvate, or stereoisomer thereof, and a pharmaceutically acceptable carrier.

Disclosed herein are pharmaceutical compositions comprising a compound of formula IV:

(IV)

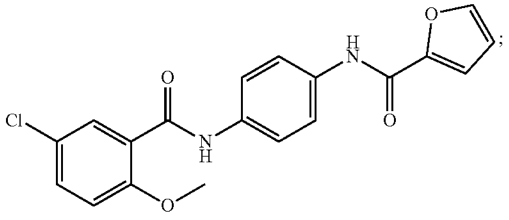

or a salt, solvate, or stereoisomer thereof, and a pharmaceutically acceptable carrier.

Disclosed herein are pharmaceutical compositions comprising a compound of formula V:

(V)

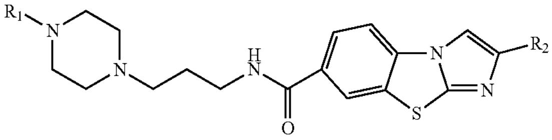

or a salt, solvate, or stereoisomer thereof, wherein $R^1$ is hydrogen, C1-C6 straight or branched alkyl, or C3-C6 cycloalkyl; and $R^2$ is phenyl, unsubstituted or substituted with $R^3$ or $OR^3$, wherein $R^3$ is hydrogen, C1-C6 straight or branched alkyl, or C3-C6 cycloalkyl, and a pharmaceutically acceptable carrier. In some embodiments, $R^1$ is C1-C4 straight or branched alkyl; and $R^2$ is phenyl substituted with $OR^3$, wherein $R^3$ is C1-C4 straight or branched alkyl. In some embodiments, the compound is (G)

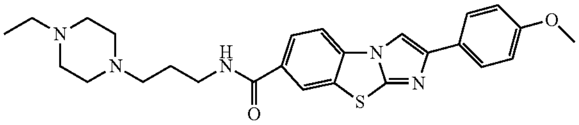

Disclosed herein are compounds of formula I:

(I)

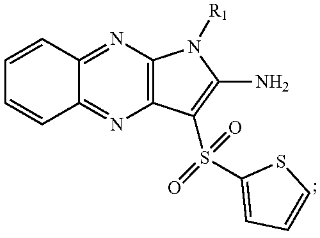

or a salt, solvate, or stereoisomer thereof, wherein $R_1$ is a cycloalkyl, heterocycloalkyl, aryl, or heteroaryl optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group, with the proviso that the compound cannot be compound A:

A)

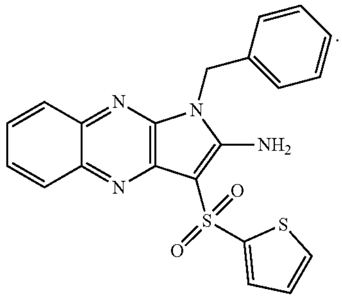

In some embodiments of the compound, or a salt, solvate, or stereoisomer thereof, the compound is selected from the group consisting of:

(B)

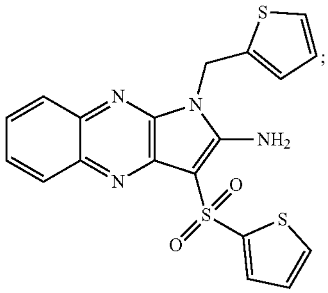

; and (C)

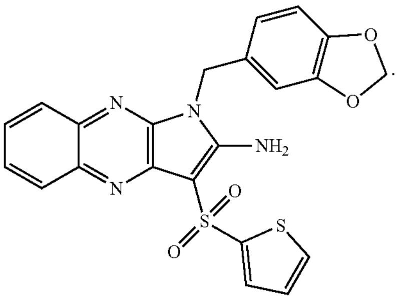

Disclosed herein are compounds of formula II:

(II)

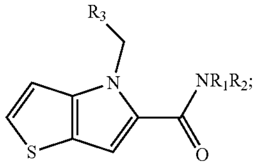

or a salt, solvate, or stereoisomer thereof, wherein $R_1$ is H, and $R_2$ is independently H or alkyl, alkenyl, alkynyl, cycloalkyl, heterocycloalkyl, aryl, or heteroaryl, optionally substituted with one or more alkyl, amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group; or $R_1$ and $R_2$ together form a $C_1$-$C_6$ heterocycloalkyl, or $C_1$-$C_6$ heteroaryl optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms; and wherein $R_3$ is H or cycloalkyl, heterocycloalkyl, aryl, or heteroaryl, optionally substituted with one or more halo, $CF_3$, CN, and $NO_2$ moieties, with the proviso that the compound cannot be a compound is selected from the group consisting of:

(D)

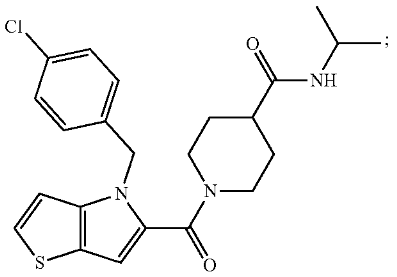

(E)

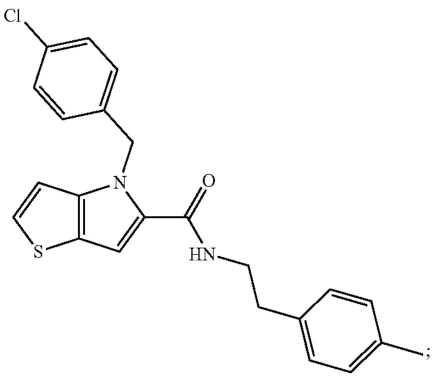

; and

-continued (F)

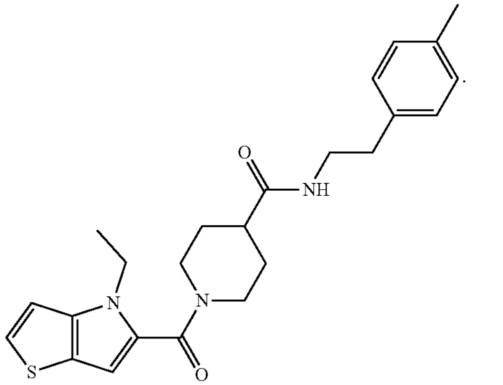

In some embodiments, $R_2$ is $C_1$-$C_6$ heterocycloalkyl or $C_1$-$C_6$ heteroaryl, optionally substituted with one or more alkyl, amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group.

Disclosed herein are compounds of formula V:

(V)

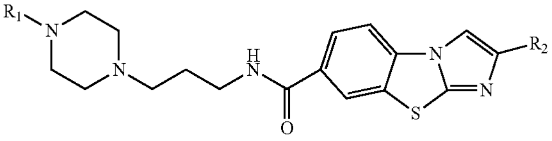

or a salt, solvate, or stereoisomer thereof, wherein $R^1$ is hydrogen, C1-C6 straight or branched alkyl, or C3-C6 cycloalkyl; and $R^2$ is phenyl, unsubstituted or substituted with $R^3$ or $OR^3$, wherein $R^3$ is hydrogen, C1-C6 straight or branched alkyl, or C3-C6 cycloalkyl. In some embodiments, $R^1$ is C1-C4 straight or branched alkyl; and $R^2$ is phenyl substituted with $OR^3$, wherein $R^3$ is C1-C4 straight or branched alkyl. In some embodiments, the compound is (G)

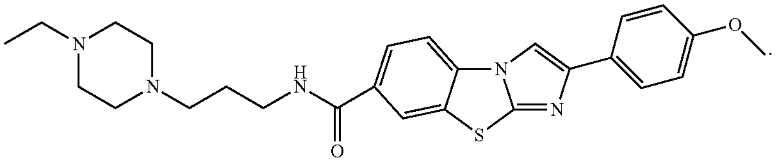

Disclosed herein are methods for the inhibition of, or treatment of, a human herpesvirus in a subject comprising administering to the subject a therapeutically effective amount of a pharmaceutically acceptable composition comprising one or more of the above described compounds and pharmaceutically acceptable carrier.

Also disclosed herein are methods for inhibition of, or treatment of, a human herpesvirus in a subject, comprising administering to the subject a therapeutically effective amount of a pharmaceutically acceptable composition comprising one or more of the above described compounds, at least one other biologically active agent, and a pharmaceutically acceptable carrier.

Also disclosed herein are uses of the compounds or compositions disclosed herein for the treatment of human herpesvirus in subjects. Also disclosed herein are the compounds or compositions disclosed herein for use in the treatment of human herpesvirus in subjects. Also disclosed herein are the use of the compounds or compositions disclosed herein for the manufacture of a medicament for treatment of human herpesvirus in subjects.

BRIEF DESCRIPTION OF THE DRAWINGS

FIG. 3B, HFFs were infected with HCMV TB40 (100 PFU/well) and treated with MLS8969 or GCV. Plaques were stained and counted after 10 days. FIG. 3C, HFFs were pretreated with 8969 or GCV for 24 h followed by infection with HCMV Towne at MOIs 1, 0.1, and 0.01. Luciferase activity was measured at 72 hpi. FIG. 3D, FIG. 3E, HFFs were pretreated with the indicated concentrations of MLS8969 or GCV for 24 h and then infected with HCMV TB40 (FIG. 3D) or GCV-resistant HCMV Towne (FIG. 3E), at 100 PFU/well. Plaques were stained and counted after 10 days. FIGS. 3A-3E Data are average±SD of triplicate values of a representative experiment. FIG. 3F, HFFs were either pre-treated or infected followed by treatment. Infection (Towne) was performed at MOI 1, 0.1 and 0.01. Expression of viral proteins from cell lysates was measured at 72 hpi. WB data are from a representative experiment.

FIG. 5A, HFFs were infected with HCMV TB40 (100 PFU/cell) and treated with indicated concentrations of compound NFU1827. Plaques were stained and counted at 8 dpi. Experiment was repeated three times and data shown are average±SD of triplicate values of a representative experiment. FIG. 5B, HFFs were infected with GCV-resistant HCMV Towne (MOI=0.1 PFU/cell) and treated with indicated concentrations of NFU1827. Luciferase activity was measured in cell lysates at 72 hpi. Data shown are average±SD of triplicate values of a representative experiment. FIGS. 5C, 5D, HFFs were infected with HCMV Towne (MOI=1 PFU/cell) and compounds were either added or removed after infection (0, 6, 12, 24, 48 72 h). Luciferase activity was measured in the cell lysates at 72 hpi. Data shown are average±SD of triplicate values of a representative experiment. FIG. 5E, HFFs were infected with HCMV Towne (MOI=1 PFU/cell) and expression of viral proteins and cellular 3-actin was determined at 72 hpi. Experiment was repeated twice, and WB data are from a representative experiment. FIGS. 5F, 5G HFFs were infected with HCMV Towne (MOI=0.1) and treated with NFU1827 (5 μM) or GCV (5 μM). Cells were lysed at indicated time points to isolate DNA. Viral DNA replication in cells (FIG. 5F), and viral DNA load in supernatants (FIG. 5G) was measured by real-time PCR. Experiment was repeated three times and data shown are average±SD of triplicate values of a representative experiment.

FIG. 6A, HFFs were infected with TB40 at 100 PFU/well and treated with indicated concentrations of MLS8554. Plaques were stained and counted at 8 dpi. Experiment was repeated three times and data from a representative experiment are shown. FIG. 6B, HFFs were infected with GCV-resistant HCMV Towne (MOI=0.1) and treated with the indicated concentrations of MLS8554. Luciferase activity was measured in cell lysates at 72 hpi. Data shown are average±SD of triplicate values from a single experiment. FIGS. 6C, 6D HFFs were infected with HCMV Towne (MOI=1) and compounds were either added or removed at the indicated time points after infection. Luciferase activity was measured in the cell lysates at 72 hpi. Experiment was repeated independently twice, and representative data from a single experiment are shown. FIG. 6E, HFFs were infected with HCMV Towne (MOI=1) and expression of viral proteins and cellular β-actin was determined after 3 days. WB data are from a representative experiment. FIGS. 6F, 6G HFFs were infected with HCMV Towne (MOI=0.1), treated with MLS8554 (2 μM) or GCV (5 μM). Supernatants were harvested and cells were lysed at indicated time points to isolate DNA. Viral DNA replication in cells (FIG. 6F), and viral DNA load in sups (FIG. 6G) were determined by real-time PCR. Data shown are average±SD of quadruplicate values from two independent experiments.

FIG. 7A, HFFs were infected with HCMV TB40 (100 PFU/well) and treated with indicated concentrations of MLS8091. Plaques were stained and counted at 8 dpi. Experiment was repeated independently three times, and data from a single representative experiment are shown. FIG. 7B, HFFs were infected with GCV-resistant HCMV Towne (MOI=0.1) and treated with indicated concentrations of MLS8091. Luciferase activity was detected in cell lysates at 72 hpi. Data shown are average±SD of triplicate values from a single experiment. FIGS. 7C, 7D HFFs were infected with HCMV Towne (MOI=1) and compounds were either added or removed at different time points after infection (0, 6, 24, 48, 72 h). Luciferase activity was measured in the cell lysates at 72 hpi. Experiment was repeated independently twice, and representative data from a single experiment are shown. FIG. 7E, HFFs were infected with HCMV Towne (MOI=1) and expression of viral proteins and cellular β-actin was determined at 72 hpi. WB data are from a representative experiment. FIGS. 7F, 7G HFFs were infected with HCMV (MOI=0.1), treated with MLS8091 (1.5 μM) or GCV (5 μM). Supernatants were harvested and cells were lysed at indicated time points to isolate DNA. Viral DNA replication in cells (FIG. 7F), and viral DNA load in sups (FIG. 7G) were determined by real-time PCR. Experiments were repeated independently twice. Data shown are average±SD of triplicate values from a single experiment.

FIG. 8A, HFFs were infected with HCMV TB40 (100 PFU/well) and treated with indicated concentrations of NCGC2955. Plaques were stained and counted at 8 dpi. Experiment was repeated independently three times, and data from a single representative experiment are shown. FIG. 8B, HFFs were infected with GCV-resistant HCMV Towne (100 PFU/well) and treated with indicated concentrations of NCGC2955. Plaques were stained and counted at 8 dpi Data shown are average±SD of triplicate values from a single experiment. FIGS. 8C, 8D HFFs were infected with HCMV Towne (MOI=1) and compounds were either added or removed at different times after infection (0, 6, 24, 48, 72 h). Luciferase activity was measured in the cell lysates at 72 hpi. Data shown are average of three independent experiments (average±SD). FIG. 8E, HFFs were infected with HCMV Towne (MOI=1) and expression of viral proteins was determined at 72 hpi. Experiment was repeated independently three times, and data from a single representative experiment are shown. FIGS. 8F, 8G HFFs were infected with HCMV Towne (MOI=0.1), treated with 2955 (3 μM) or GCV (5 μM). Supernatants were harvested and cells were lysed at indicated time points to isolate DNA. Viral DNA replication in cells (FIG. 8F), and viral DNA load in sups (FIG. 8G) were determined by real-time PCR. Data shown are average±SD of quadruplicate values from two independent experiments.

(FIGS. 9A-9E) HFFs were infected with HCMV Towne (MOI=1) and treated with each compound alone, and combination of each compound with GCV at different doses. For drug combination HCMV-infected cells were treated with starting drug concentration of two times the $EC_{50}$ value of individual compound and two-fold serial dilutions. Luciferase activity was detected in cell lysates at 72 hpi and antiviral activity of compounds in drug combination was calculated by Bliss Model. Solid lines with indicate observed HCMV inhibition (dose response) and dotted lines indicate expected HCMV inhibition at each dose of drug combination. FIGS. 9A-9D Experiments were repeated three times independently. Data from a single representative experiment are shown. FIG. 9E, Data shown are average±SD of triplicate values from a single experiment.

(FIGS. 10A-10E) HFFs were infected with TB40 (100 PFUs/well) and treated with each compound alone, and combination of each compound with letermovir at different doses. For drug combination HCMV-infected cells were treated with starting concentration of two times the $EC_{50}$ value of individual compound followed by two-fold serial dilutions. The number of plaques in each condition was counted at 10 dpi and antiviral activity of compounds was calculated using the Bliss Model. Solid lines indicate observed HCMV inhibition (dose response) and dotted lines indicate expected HCMV inhibition at each dose of drug combination. Data shown are average±SD of triplicate values from a single experiment.

DETAILED DESCRIPTION OF THE INVENTION

Figure 1:
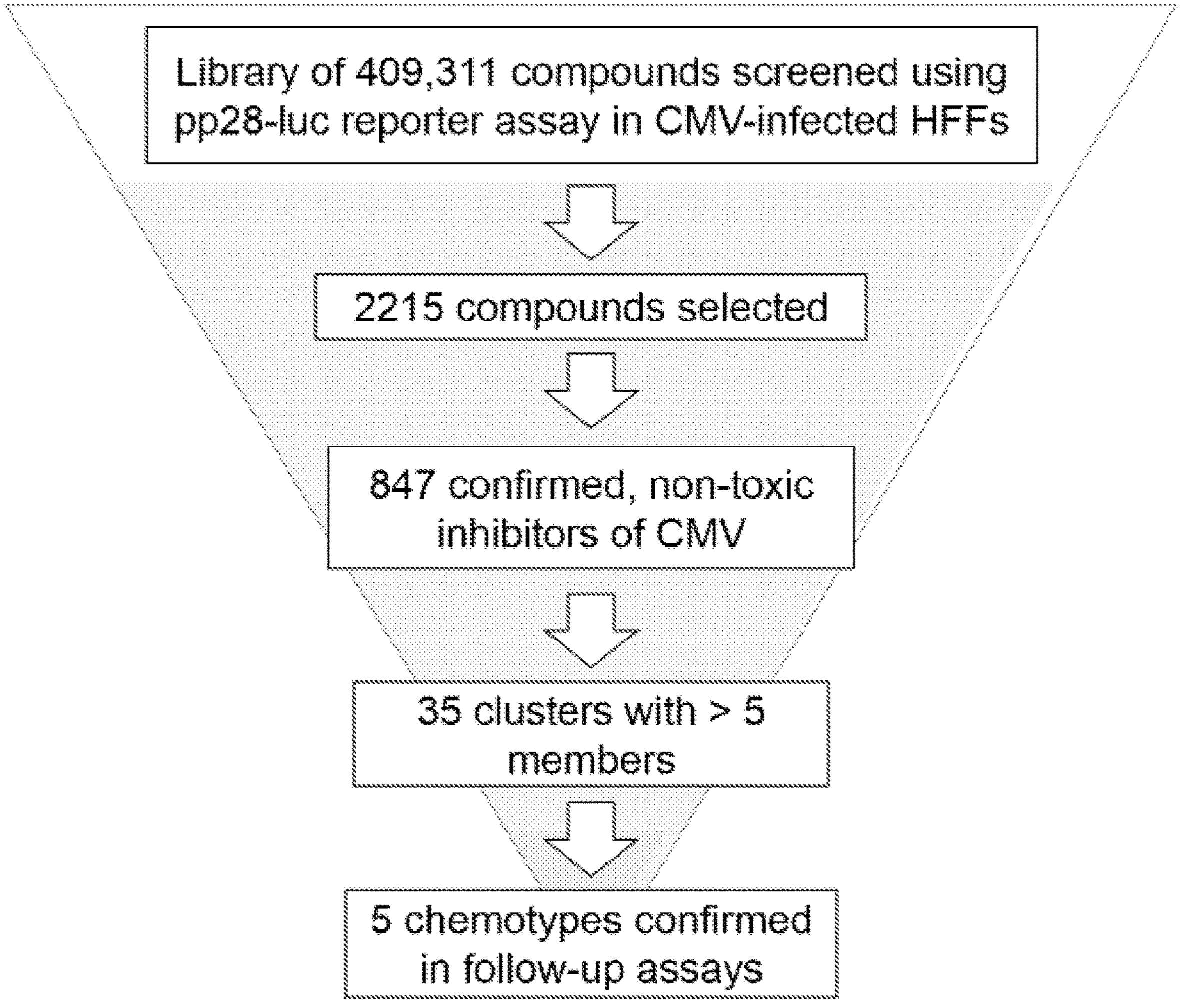
FIG. 1. Flow chart of high throughput screening (HTS).
Figure 2:
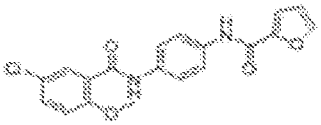
FIG. 2. Chemical structure and MW of the five compounds.
Figure 2:
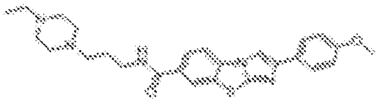
Figure 2:
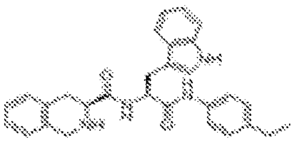
Figure 2:
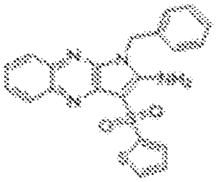
Figure 2:
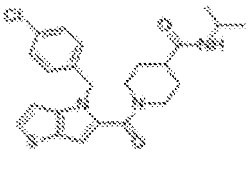

There is a need to improve the currently available herpesvirus drugs. Towards this goal, a large screening campaign of ~400,000 compounds using a highly-sensitive pp28-luciferase HCMV reporter and several collections of chemical libraries[20] was performed.

Disclosed herein are compounds and pharmaceutical compositions for use in the prophylaxis and treatment of human herpes virus in a subject in need thereof.

The compounds described herein inhibit the human herpes when administered to a cell or population of cells in an effective amount. In certain embodiments, the cell, or population of cells, are within a host organism or subject.

As used herein, the term "human herpesvirus" means DNA viruses from the family Herpesviridae, which are known to infect humans. Examples of species of Herpesviridae include, HSV-1, which causes facial cold-sores (HHV-1), HSV-2 (genital herpes) (HHV-2), Varicella zoster virus, which causes chicken-pox and shingles (HHV-3), Epstein-Barr virus, which causes mononucleosis (HHV-4), HCMV or human cytomegalovirus (CMV or HHV-5), Roseolovirus (HHV-6A), Herpes lymphotrophic virus (HHV-6B), *Pityriasis rosea* (HHV-7), and Kaposi's sarcoma-associated herpesvirus (HHV-8).

Disclosed herein are compounds of formulas I-V which are useful in the inhibition of viral diseases. In some embodiments, the compounds of formulas I-V are useful in the inhibition of herpes virus infections in subjects in need thereof, including mammals, such as humans, e.g., infants, children, and adults, including adults 40 years old and older.

Also disclosed herein are pharmaceutical compositions comprising compounds of formulas I-V, and a pharmaceutical carrier, which are useful in the inhibition of viral diseases. In some embodiments, the pharmaceutical compositions are useful in the inhibition of herpes virus infections in mammals, including humans.

In accordance with one or more embodiments, disclosed herein are pharmaceutical compositions comprising compounds of formulas I-V, at least one additional biologically active agent, and a pharmaceutical carrier, which are useful in the inhibition of viral diseases. In some embodiments, the pharmaceutical compositions are useful in the inhibition of herpes virus infections in mammals, including humans.

In accordance with one or more embodiments, disclosed herein are methods for inhibition of human herpes virus in a subject comprising administering to the subject a therapeutically effective amount of a compound of formulas I-V or a pharmaceutically acceptable composition comprising a compound of formulas I-V and pharmaceutically acceptable carrier.

Disclosed herein are methods of inhibiting human herpesviruses in a subject in need thereof, comprising administering to the subject a compound of formula I or a pharmaceutical composition thereof comprising a pharmaceutically acceptable carrier:

(I)

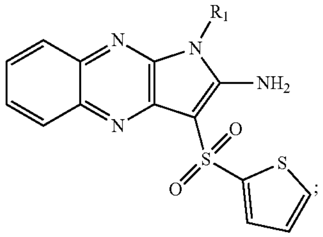

or a salt, solvate, or stereoisomer thereof, wherein $R_1$ is a cycloalkyl, heterocycloalkyl, aryl, or heteroaryl optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group. In some embodiments, the compound is selected from the group consisting of:

(A)

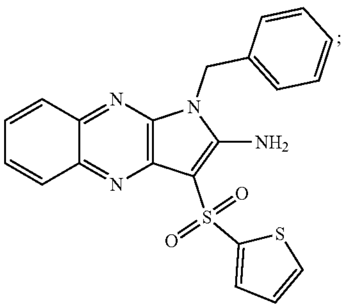

(B)

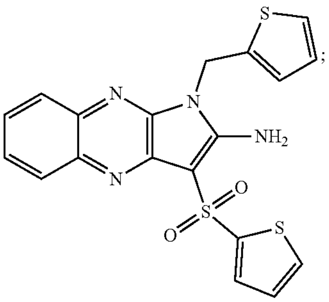

and (C)

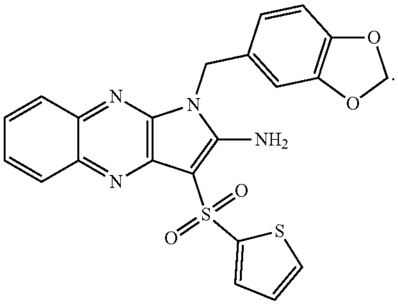

Disclosed herein are methods of inhibiting human herpesviruses in a subject in need thereof, comprising administering to the subject a compound of formula II or a pharmaceutical composition thereof comprising a pharmaceutically acceptable carrier:

(II)

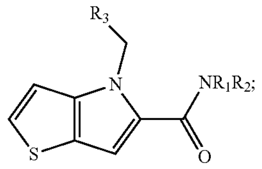

or a salt, solvate, or stereoisomer thereof, wherein $R_1$ is H, and $R_2$ is independently H or alkyl, alkenyl, alkynyl, cycloalkyl, heterocycloalkyl, aryl, or heteroaryl, optionally substituted with one or more alkyl, amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group; or $R_1$ and $R_2$ together form a $C_1$-$C_6$ heterocycloalkyl, or $C_1$-$C_6$ heteroaryl optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms; and wherein $R_3$ is H or cycloalkyl, heterocycloalkyl, aryl, or heteroaryl, optionally substituted with one or more halo, $CF_3$, CN, and $NO_2$ moieties. In some embodiments, $R_2$ is $C_1$-$C_6$ heterocycloalkyl or $C_1$-$C_6$ heteroaryl, optionally substituted with one or more alkyl, amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group. In some embodiments, the compound is selected from the group consisting of:

(D)

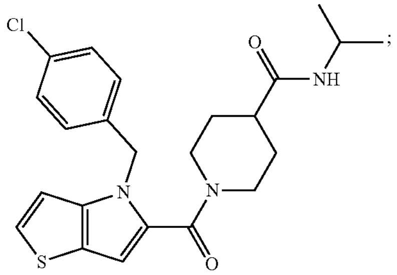

(E)

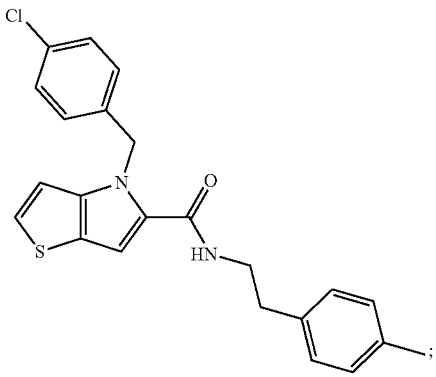

; and

-continued (F)

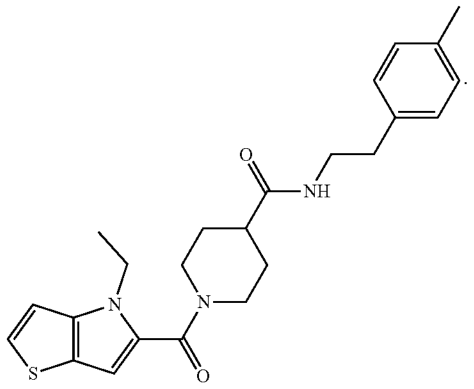

Disclosed herein are methods of inhibiting human herpesviruses in a subject in need thereof, comprising administering to the subject a compound of formula III or a pharmaceutical composition thereof comprising a pharmaceutically acceptable carrier:

(III)

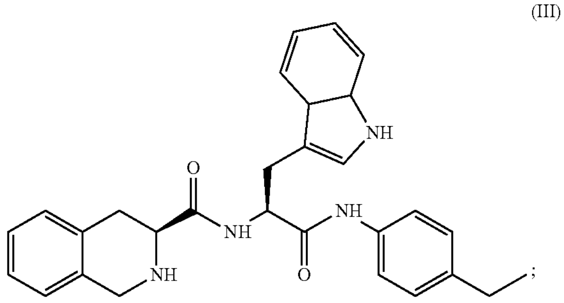 [SMILES: CCc1ccc(NC(=O)[C@H](CC2=CNC3C=CC=CC23)NC(=O)[C@@H]2Cc3ccccc3CN2)cc1]

or a salt, solvate, or stereoisomer thereof.

Disclosed herein are methods of inhibiting human herpesviruses in a subject in need thereof, comprising administering a compound of formula IV or a pharmaceutical composition thereof comprising a pharmaceutically acceptable carrier:

(IV)

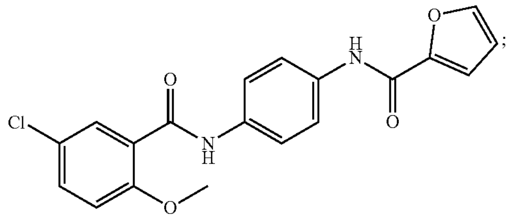

or a salt, solvate, or stereoisomer thereof.

Disclosed herein are methods of inhibiting human herpesviruses in a subject in need thereof, comprising administering to the subject a compound of formula V or a pharmaceutical composition thereof comprising a pharmaceutically acceptable carrier:

(V)

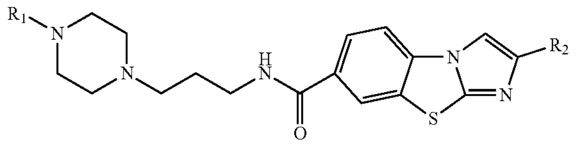

or a salt, solvate, or stereoisomer thereof, wherein $R^1$ is hydrogen, C1-C6 straight or branched alkyl, or C3-C6 cycloalkyl; and $R^2$ is phenyl, unsubstituted or substituted with $R^3$ or $OR^3$, wherein $R^3$ is hydrogen, C1-C6 straight or branched alkyl, or C3-C6 cycloalkyl. In some embodiments, $R^1$ is C1-C4 straight or branched alkyl; and $R^2$ is phenyl substituted with $OR^3$, wherein $R^3$ is C1-C4 straight or branched alkyl. In some embodiments, the compound is (G)

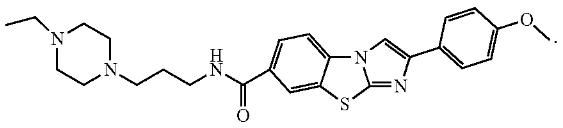

In some embodiments, the methods disclosed herein further comprise administering more than one biologically active agent.

In some embodiments, the herpesvirus is selected from the group consisting of human herpesvirus 1 (HHV-1), human herpesvirus 2 (HHV-2), human herpesvirus 3 (HHV-3), human herpesvirus 4 (HHV-4), human herpesvirus 5 (CMV or HHV-5), human herpesvirus 6 (HHV-6), human herpesvirus 7 (HHV-7), and human herpesvirus 8 (HHV-8). In some embodiments, the herpesvirus is HHV-5.

Disclosed herein are pharmaceutical compositions comprising a compound of formula I:

(I)

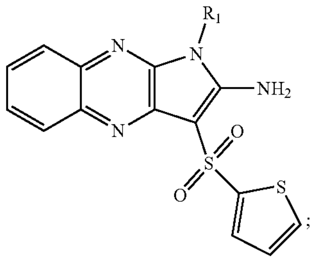

;

or a salt, solvate, or stereoisomer thereof, wherein $R_1$ is a cycloalkyl, heterocycloalkyl, aryl, or heteroaryl optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group, and a pharmaceutically acceptable carrier. In some embodiments, the compounds are selected from the group consisting of:

(A)

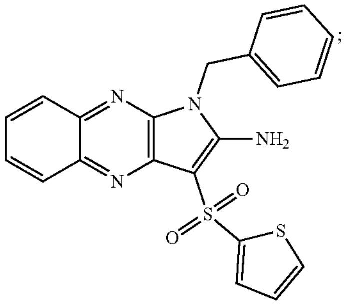

;

(B)

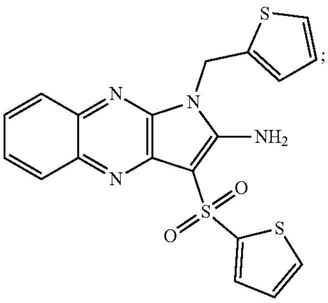

; and (C)

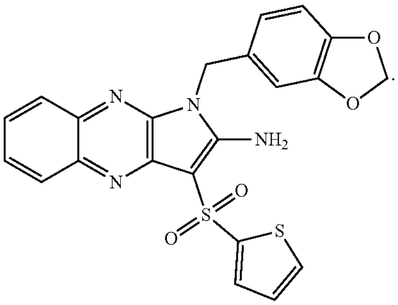

.

Disclosed herein are pharmaceutical compositions comprising a compound of formula II:

(II)

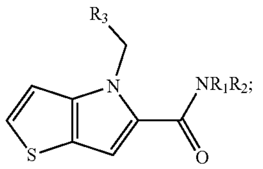

or a salt, solvate, or stereoisomer thereof, wherein $R_1$ is H, and $R_2$ is independently H or alkyl, alkenyl, alkynyl, cycloalkyl, heterocycloalkyl, aryl, or heteroaryl, optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group; or $R_1$ and $R_2$ together form a $C_1$-$C_6$ heterocycloalkyl, or $C_1$-$C_6$ heteroaryl optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms; and wherein $R_3$ is H or cycloalkyl, heterocycloalkyl, aryl, or heteroaryl, optionally substituted with one or more halo, $CF_3$, CN, and $NO_2$ moieties. In some embodiments, R2 is $C_1$-$C_6$ heterocycloalkyl or $C_1$-$C_6$ heteroaryl, optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group. In some embodiments, the compound is selected from the group consisting of (D)

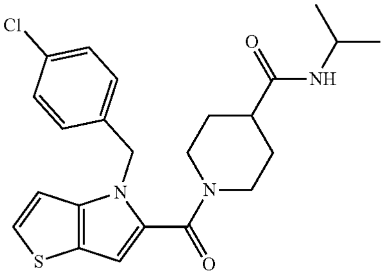
;

(E)

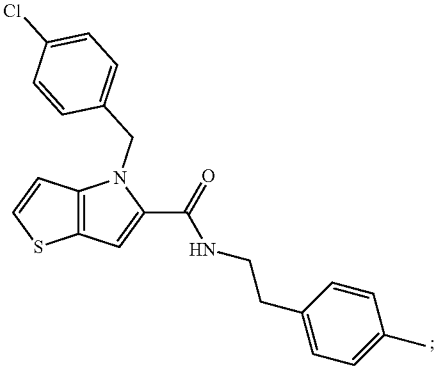
; and (F)

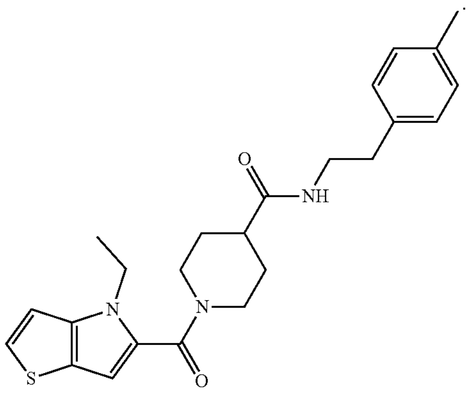
.

Disclosed herein are pharmaceutical compositions comprising a compound of formula III:

(III)

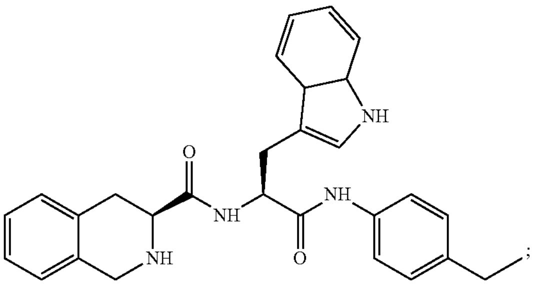
;

or a salt, solvate, or stereoisomer thereof, and a pharmaceutically acceptable carrier.

Disclosed herein are pharmaceutical compositions comprising a compound of formula IV:

(IV)

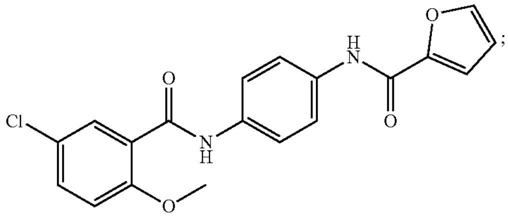
;

or a salt, solvate, or stereoisomer thereof, and a pharmaceutically acceptable carrier.

Disclosed herein are pharmaceutical compositions comprising a compound of formula V:

(V)

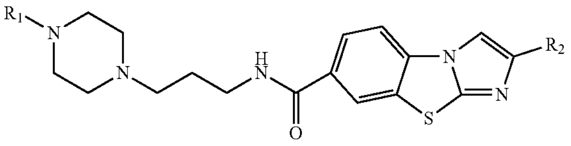

or a salt, solvate, or stereoisomer thereof, wherein $R^1$ is hydrogen, C1-C6 straight or branched alkyl, or C3-C6 cycloalkyl; and $R^2$ is phenyl, unsubstituted or substituted with $R^3$ or $OR^3$, wherein $R^3$ is hydrogen, C1-C6 straight or branched alkyl, or C3-C6 cycloalkyl, and a pharmaceutically acceptable carrier. In some embodiments, $R^1$ is C1-C4 straight or branched alkyl; and $R^2$ is phenyl substituted with $OR^3$, wherein $R^3$ is C1-C4 straight or branched alkyl. In some embodiments, the compound is (G)

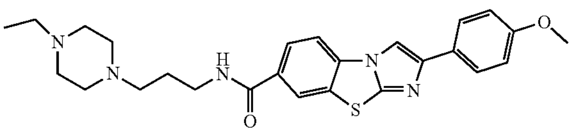

Disclosed herein are compounds of formula I:

(I)

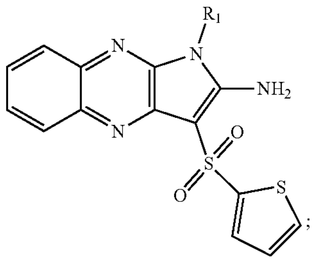

or a salt, solvate, or stereoisomer thereof, wherein $R_1$ is a cycloalkyl, heterocycloalkyl, aryl, or heteroaryl optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group, with the proviso that the compound cannot be compound A:

A)

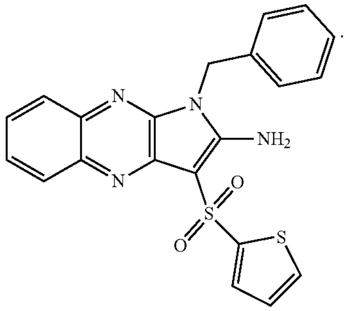

In some embodiments of the compound, or a salt, solvate, or stereoisomer thereof, the compound is selected from the group consisting of:

(B)

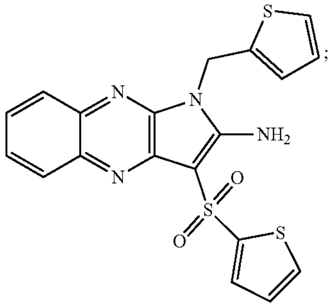

; and

-continued (C)

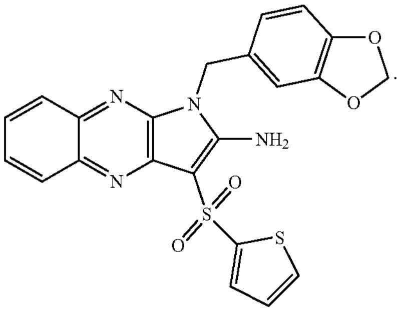

Disclosed herein are compounds of formula II:

(II)

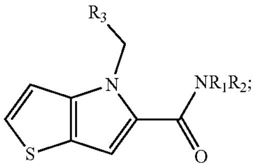

or a salt, solvate, or stereoisomer thereof, wherein $R_1$ is H, and $R_2$ is independently H or alkyl, alkenyl, alkynyl, cycloalkyl, heterocycloalkyl, aryl, or heteroaryl, optionally substituted with one or more alkyl, amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group; or $R_1$ and $R_2$ together form a $C_1$-$C_6$ heterocycloalkyl, or $C_1$-$C_6$ heteroaryl optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms; and wherein $R_3$ is H or cycloalkyl, heterocycloalkyl, aryl, or heteroaryl, optionally substituted with one or more halo, $CF_3$, CN, and $NO_2$ moieties, with the proviso that the compound cannot be a compound is selected from the group consisting of:

(D)

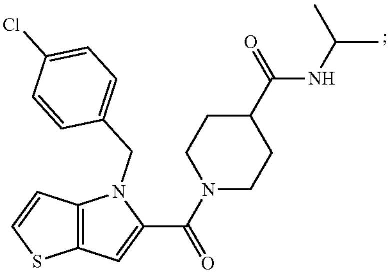

-continued (E)

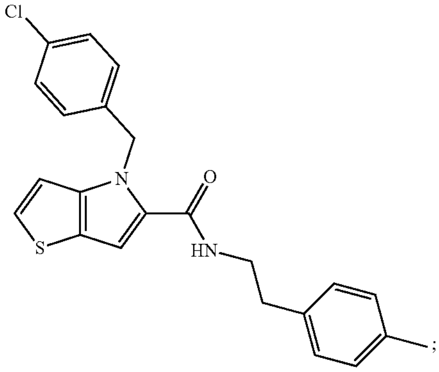

; and (F)

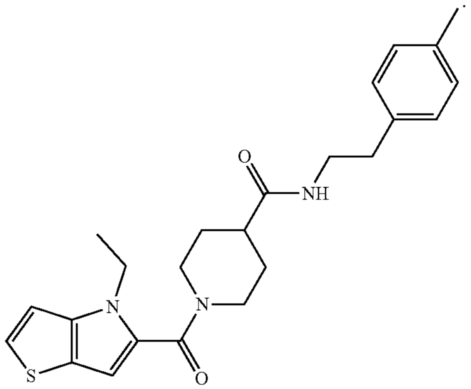

In some embodiments, $R_2$ is $C_1$-$C_6$ heterocycloalkyl or $C_1$-$C_6$ heteroaryl, optionally substituted with one or more alkyl, amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group.

Disclosed herein are compounds of formula V:

(V)

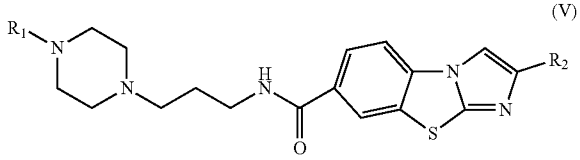

or a salt, solvate, or stereoisomer thereof, wherein $R^1$ is hydrogen, C1-C6 straight or branched alkyl, or C3-C6 cycloalkyl; and $R^2$ is phenyl, unsubstituted or substituted with $R^3$ or $OR^3$, wherein $R^3$ is hydrogen, C1-C6 straight or branched alkyl, or C3-C6 cycloalkyl. In some embodiments, $R^1$ is C1-C4 straight or branched alkyl; and $R^2$ is phenyl substituted with $OR^3$, wherein $R^3$ is C1-C4 straight or branched alkyl. In some embodiments, the compound is (G)

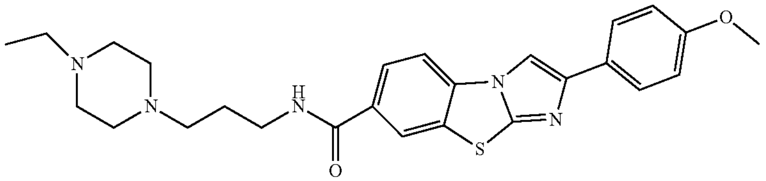

.

The term "aliphatic" is an art-recognized term and includes linear, branched, and cyclic alkanes, alkenes or alkynes. In certain embodiments, aliphatic groups are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer carbon atoms. Likewise cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls," the latter of which refers to alkyl moieties having substituents replacing hydrogen on one or more carbons of the hydrocarbon backbone. Such substituents can include, for example, a halogen, a hydroxyl, a carbonyl (such as a carboxyl, an alkoxycarbonyl, a formyl or an acyl), a thiocarbonyl (such as a thioester, a thioacetate, or a thioformate), an alkoxyl, a phosphoryl, a phosphonate, a phosphinate, an amino, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For example, the substituents of a substituted alkyl can include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $-CF_3$, —CN and the like. Exemplary substituted alkyls are described below. Cycloalkyls can be further substituted with alkyls, alkenyls, alkoxys, alkylthios, aminoalkyls, carbonyl-substituted alkyls, $-CF_3$, —CN and the like.

The term "aralkyl" is art-recognized, and includes aryl groups (e.g., an aromatic or heteroaromatic group).

The terms "alkenyl" and "alkynyl" are art-recognized, and refer respectively to moieties containing at least one double or triple bond.

The term "aryl" is art-recognized, and includes 5-, 6-, and 7-membered single ring aromatic groups that can include from zero to four heteroatoms, for example, benzene, pyrole, furan, thiophene, imidazole, oxazole, thiazole, triazole, pyrazole, pyridine, pyrazine, pyridazine and pyrimidine, and the like. The term "heteroatom" generally includes an atom of any element other than carbon or hydrogen. Illustrative heteroatoms include boron, nitrogen, oxygen, phosphorus, sulfur, and selenium. Aryl groups having heteroatoms in the ring structure can also be referred to as "aryl heterocycles"

or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydyl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls, and/or heterocyclyls, or rings joined by non-cyclic moieties.

The terms "ortho," "meta" and "para" are art-recognized and apply to 1,2-, 1,3- and 1,4-disubstituted benzene rings, respectively. For example, the names 1,2-dimethylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles can also be polycycles. Heterocyclic groups include, for example, thiophene, thianthrene, furan, pyran, isobenzofuran, chromene, xanthene, phenoxanthin, pyrrole imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphtyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones and the like. The heterocyclic ring can be substituted at one or more positions with such substituents as described above, as for example, halogen, alkyl aralkyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CD_3$, —CN or the like.

The terms "polycyclyl" and polycyclic group" are art-recognized and include structures with two or more rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms, e.g., three or more atoms are common to both rings, are termed "bridged" rings. Each of the rings of the polycycle can be substituted with such substituents as described above, as for example, halogen, alkyl, aralkyl, alkenyl, alkynyl, cycloalkyl, hyroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CD_3$, —CN or the like.

The term "carbocycle" is art-recognized and includes an aromatic or non-aromatic ring in which each atom of the ring is carbon. The following art-recognized terms have the following meanings: "nitro" means —$NO_2$; the term "halogen" designates —F, —Cl, —Br, or —I; the term "sulfhydryl" means —SH; the term "hydroxyl" or "hydroxy" means —OH; and the term sulfonyl" means —$SO_2$—.

The terms "amine" and "amino" are art-recognized and include both unsubstituted and substituted amines. A primary amine carries two hydrogens, a secondary amine, one hydrogen and another substituent and a tertiary amine, the two hydrogens are substituted. The substituents for one or both of the hydrogens can be, for example, and alkyl, an alkenyl, and aryl, a cycloalkyl, a cycloalkenyl, a heterocycle, a polycycle and so on. If both hydrogens are substituted with carbonyls, the carbonyl framed nitrogen forms an imide.

The term "alkylamine" includes an amine group, as defined above, having a substituted or unsubstituted alkyl attached thereto.

The term "amido" is art-recognized as an amino-substituted carbonyl.

The term "alkylthio" is art-recognized and includes and alkyl group, as defined above, having a sulfur radical attached thereto. In certain embodiments, the "alkylthio" moiety is represented by one of —S-alkyl, —S-alkenyl, —S-alkynyl and so on. Representative alkylthio groups include methylthio, ethylthio and the like.

The term "carbonyl" is art-recognized and includes a C═O structure. Carbonyls are involved in esters; carboxyl groups; formates; thiocarbonyls; thioesters; thiocarboxylic acids; thioformates; ketones; and aldehydes.

The terms "alkoxyl" and "alkoxy" are art-recognized and include an alkyl group, as defined above, having an oxygen radical attached thereto. Representative alkoxyl groups include methoxy, ethoxy, propyloxy, tert-butoxy and the like.

An "ether" is two hydrocarbons covalently linked by an oxygen. Accordingly, the substituent of an alkyl that renders that alkyl an ether is or resembles an alkoxyl, such as represented by one of —O-alkyl, —O-alkenyl, —O-alkynyl and so on.

The term "sulfonate" is art-recognized and includes a moiety wherein a sulfur atom carries two double bonded oxygens and a single bonded oxygen.

The term "sulfate" is art-recognized and includes a moiety that resembles a sulfonate but includes two single bonded oxygens.

The terms "sulfonamide," "sulfamoyl," "sulfonyl," and "sulfoxido" are art-recognized and each can include a variety of R group substituents as described herein.

The terms "phosphoramidite" and "phophonamidite" are art-recognized.

The term "selenoalkyl" is art-recognized and includes an alkyl group having a substituted seleno group attached thereto. Exemplary "selenoethers" which can be substituted on the alkyl are selected from one of —Se-alkyl, —Se-alkenyl, —Se-alkynyl and so on.

Substitutions can be made to alkenyl and alkynyl groups to produce, for example, aminoalkenyls, aminoalkynyls, amidoalkenyls, iminoalkenyls, iminoalkynyls, thioalkenyls, thioalkynyls, carbonyl-substituted alkenyls or alkynyls.

A hydrocarbon is an art recognized term and includes all permissible compounds having at least one hydrogen and one carbon atom. For example, permissible hydrocarbons include acyclic and cyclic, branched and unbranched, carbocyclic and heterocyclic, aromatic and nonaromatic organic compounds that can be substituted or unsubstituted.

The phrase "protecting group" is art-recognized and includes temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed, Greene et al., Protective Groups in Organic Synthesis 2nd ed., Wiley, New York, (1991), for example.

The definition of each expression, e.g., alkyl, aryl etc., when it occurs more than once in any structure, is intended to be independent of its definition elsewhere in the same structure unless otherwise indicated expressly or by the context.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms are art-recognized and represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Accordingly, included within the compounds disclosed herein are the tautomeric forms of the disclosed compounds, isomeric forms including enantiomers, stereoisomers, and diastereoisomers, and the pharmaceutically-acceptable salts thereof. The term "pharmaceutically acceptable salts" embraces salts commonly used to form alkali metal salts and to form addition salts of free acids or free bases. Examples of acids which can be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds disclosed here include, for example, acid addition salts which can, for example, be formed by mixing a solution of the compound disclosed herein with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts can be prepared by conventional means by reacting, for example, the appropriate acid or base with the corresponding compounds disclosed herein.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds disclosed herein should be pharmaceutically acceptable salts. Other salts can, however, be useful in the preparation of the compounds disclosed herein or of their pharmaceutically acceptable salts.

In addition, embodiments disclosed herein include hydrates of the compounds disclosed herein. The term "hydrate" includes but is not limited to hemihydrate, monohydrate, dihydrate, trihydrate and the like. Hydrates of the compounds disclosed herein can be prepared by contacting the compounds with water under suitable conditions to produce the hydrate of choice.

Embodiments disclosed herein also include a process for preparing pharmaceutical products comprising the compounds. The term "pharmaceutical product" means a composition suitable for pharmaceutical use (pharmaceutical composition), as defined herein. Pharmaceutical compositions formulated for particular applications comprising the compounds disclosed herein are to be considered embodiments thereof.

The compositions disclosed herein can include a carrier. The term "carrier" refers to a diluent, adjuvant, excipient or vehicle with which the therapeutic is administered.

With respect to pharmaceutical compositions described herein, the pharmaceutically acceptable carrier can be any of those conventionally used, and is limited only by physicochemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein can be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers can be, for example, aqueous or non-aqueous solutions, suspensions, emulsions or oils. Examples of non-aqueous solvents are propylene glycol, polyethylene glycol, injectable organic cosolvents, surfactants, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, saline solution, Ringer's dextrose, dextrose and sodium chloride, lactated Ringer's and fixed oils. Formulations suitable for parenteral administration include, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol can be the liquid carriers, particularly for injectable solutions.

In addition, in some embodiments, the compounds disclosed herein can further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical compositions disclosed herein. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route. In some embodiments, in the methods disclosed herein, the compound or pharmaceutical composition disclosed herein is administered orally, e.g., as a tablet, capsule, or suspension, or intravenously.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers can be used. In order to minimize or eliminate irritation at the site of injection, such compositions can contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the disclosure herein. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

The amount or dose of the compounds, salts, solvates, or stereoisomers of any one the compounds of Formula I, II, III, IV, and V, as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

The dose of the compounds, salts, solvates, or stereoisomers of any one the compounds of Formula I, II, III, IV, and V, as set forth above, disclosed herein also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the disclosure herein, the dose of the compound can be about 0.001 to about 1000 mg/kg body weight of the subject being treated/day.

In some embodiments, the term "administering" means that the compounds disclosed herein are introduced into a subject, e.g., a subject receiving treatment for a disease, and the compounds are allowed to come in contact with the one or more disease related cells or population of cells in vivo. In some embodiments the host cell or population of cells in the host can be any cell or population of cells that can be selectively bound by the antigens bound to the compounds of formula I, II, III, IV, and V described above. One of ordinary skill in the art would understand the host cells can be cells infected with a virus.

In accordance with some embodiments, the disclosure herein provides methods for inhibition of human herpes virus in a subject comprising administering to the subject a therapeutically effective amount of a pharmaceutically acceptable composition comprising one or more of the above described compounds and pharmaceutically acceptable carrier.

In accordance with some embodiments, the disclosure herein provides methods for treating medical conditions including but not limited to inhibition of human herpes virus in a subject comprising administering to the subject a therapeutically effective amount of a pharmaceutically acceptable composition comprising one or more of the above described compounds, a pharmaceutically acceptable carrier, and at least one additional biologically active agent.

In accordance with some embodiments, the disclosure herein provides methods for the inhibition of, or treatment of, human herpes virus in a subject comprising administering to the subject a therapeutically effective amount of a pharmaceutically acceptable composition comprising one or more of the above described compounds and pharmaceutically acceptable carrier.

In accordance with yet other embodiments, the disclosure herein provides methods for inhibition of, or treatment of, human herpes virus, such as inhibition of human herpesvirus replication, in a subject comprising administering to the subject a therapeutically effective amount of a pharmaceutically acceptable composition comprising one or more of the above described compounds, at least one biologically active agent, and pharmaceutically acceptable carrier.

"Inhibiting herpesvirus" or "inhibition of herpesvirus" means decreasing or preventing viral replication, treatment of symptoms caused by viral infection, such as, e.g., hepatitis or pneumonitis, decrease viral load measured in blood or plasma, and/or decrease persistent viremia.

"Treating" or "treatment" is an art-recognized term which includes curing as well as ameliorating at least one symptom of any condition or disease. Treating includes reducing the likelihood of a disease, disorder or condition from occurring in an animal which can be predisposed to the disease, disorder and/or condition but has not yet been diagnosed as having it; inhibiting the disease, disorder or condition, e.g., impeding its progress; and relieving the disease, disorder or condition, e.g., causing any level of regression of the disease; inhibiting the disease, disorder or condition, e.g., impeding its progress; and relieving the disease, disorder or condition, even if the underlying pathophysiology is not affected or other symptoms remain at the same level.

In some embodiments, the pharmaceutical compositions disclosed herein are useful for treating viral infections in a subject. In some embodiments, the viral infection is a herpes virus infection, e.g., CMV infection.

In some embodiments, the pharmaceutical compositions disclosed herein can be combined with one or more additional biologically active agents, including, for example, anti-viral agents.

"Prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The biologically active agent can vary widely with the intended purpose for the composition. The term active is art-recognized and refers to any moiety that is a biologically, physiologically, or pharmacologically active substance that acts locally or systemically in a subject. Examples of biologically active agents, that can be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent can be used which are capable of being released the subject composition, for example, into adjacent tissues or fluids upon administration to a subject. In some embodiments, a biologically active agent can be used in cross-linked polymer matrix to, for example, promote cartilage formation. In other embodiments, a biologically active agent can be used in cross-linked polymer matrix to treat, ameliorate, inhibit, or prevent a disease or symptom, in conjunction with, for example, promoting cartilage formation.

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compounds and compositions disclosed herein.

In certain embodiments, the subject compositions comprise about 1% to about 75% or more by weight of the total composition, alternatively about 2.5%, 5%, 10%, 20%, 30%, 40%, 50%, 60% or 70%, of a biologically active agent.

Non-limiting examples of biologically active agents include following: adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheal, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and prodrugs.

Specific examples of useful biologically active agents the above categories include: (a) anti-neoplastics such as androgen inhibitors, antimetabolites, cytotoxic agents, and immunomodulators; (b) anti-tussives such as dextromethorphan, hydrobromide, noscapine, carbetapentane citrate, and chlophedianol hydrochloride; (c) antihistamines such as chlorpheniramine phenindamine tartrate, pyrilamine doxylamine succinate, and phenyltoloxamine citrate; (d) decongestants such as hydrochloride, phenylpropanolamine hydrochloride, pseudoephedrine hydrochloride, and ephedrine; (e) various alkaloids such as codeine phosphate, codeine sulfate, and morphine; (f) mineral supplements such as potassium chloride, zinc chloride, calcium carbonate, magnesium oxide, and other alkali metal and alkaline earth metal salts; (g) ion exchange resins such as such as N-acetyl-procainamide; (i) antipyretics and analgesics such as acetaminophen, aspirin and ibuprofen; appetite suppressants such as phenyl-propanol amine or caffeine; (k) expectorants such as guaifenesin; (1) antacids such as aluminum hydroxide and magnesium hydroxide; biologicals such as peptides, polypeptides, proteins and amino acids, hormones, interferons or cytokines and other bioactive peptidic compounds, such as calcitonin, ANF, EPO and insulin; (n) anti-infective agents such as anti-fungals, anti-virals, antiseptics and antibiotics; and (m) desensitizing agents and antigenic materials, such as those useful for vaccine applications.

More specifically, non-limiting examples of useful biologically active agents include the following therapeutic categories: analgesics, such as nonsteroidal anti-inflammatory drugs, opiate agonists and salicylates; antihistamines, such as H1-blockers and H2-blockers; anti-infective agents, such as antihelmintics, antianaerobics, antibiotics, aminoglycoside antibiotics, antifungal antibiotics, cephalosporin antibiotics, macrolide antibiotics, miscellaneous antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and *vinca* alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, a-blocker sympatholytics, sympatholytics, sympathomimetics, and adrenergic agonist sympathomimetics; cardiovascular agents, such as antianginals, antianginals, calcium-channel blocker antianginals, nitrate antianginals, antiarrhythmics, cardiac glycoside antiarrhythmics, class I antiarrhythmics, class antiarrhythmics, class antiarrhythmics, class IV antiarrhythmics, antihypertensive agents, a-blocker antihypertensives, angiotensin-converting enzyme inhibitor (ACE inhibitor) antihypertensives, 13-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, reductase inhibitor antilipemics, inotropes, cardiac glycoside inotropes, and thrombolytic agents; dermatological agents, such as antihistamines, anti¬,inflammatory agents, corticosteroid anti-inflammatory agents, anesthetics, topical anti¬infectives, topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti¬inflammatory agents, antacid anti-ulcer agents, gastric acid-pump inhibitor anti-ulcer agents, gastric mucosal anti-ulcer agents, H2-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immunosuppressive anti-inflammatory agents, nonsteroidal anti¬inflammatory drugs, salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, anti-glaucoma agents, mitotics, anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti¬inflammatory agents, and ophthalmic nonsteroidal anti-inflammatory drugs; psychotropic agents, such as antidepressants, heterocyclic antidepressants, monoamine oxidase inhibitors selective serotonin re-uptake inhibitors tricyclic antidepressants, antimanics, anti-psychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti¬inflammatory agents, and respiratory corticosteroid anti-intlammatory agents; toxicology agents, such as antidotes, heavy agents, substance abuse agents, deterrent substance abuse agents, and withdrawal substance abuse agents; minerals; and vitamins, such as vitamin A, vitamin B, vitamin C, vitamin D, vitamin E, and vitamin K.

Other classes of biologically active agents from the above categories include: (1) analgesics in general, such as lidocaine, other "caine" analgesics or derivatives thereof, and nonsteroidal anti-intlammatory drugs (NSAIDs) analgesics, including diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) H1-blocker antihistamines, such as clemastine and terfenadine; (5) H2-blocker antihistamines, such as cimetidine, famotidine, nizadine, and ranitidine; (6) anti-infective agents, such as mupirocin; (7) antianaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous antibiotic anti-infectives, such as and imipenem; penicillin, (11) antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline and tetracycline; (14) antituberculosis antimycobacterial anti-infectives such as isoniazid and rifampin; (15) anti-protozoal anti-infectives, such as atovaquone and dapsone; (16) antimalarial anti-protozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon-7, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antineoplastic agents, such as fluorouracil (S-FU) and gemcitabine; (23) hormonal antineoplastics, such as goserelin, leuprolide, and tamoxifen; (24) natural antineoplastics, such as aldesleukin, interleukin-2, docetaxel, etoposide, interferon; paclitaxel, other taxane derivatives, and tretinoin (ATRA); (25) antibiotic natural antineoplastics, such as bleomycin, dactinomycin, daunorubicin, doxorubicin, and mitomycin; (26) *vinca* alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) a-blocker sympatholytics, such as prazosin; (34) D-blocker sympatholytics, such as atenolol; (35) adrenergic sympathomimetics, such as albuterol and dobutamine; (36) cardiovascular agents, such as aspirin (ASA) (enteric coated ASA); (37) D-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as (41) class I antiarrhythmics, such as lidocaine, mexiletine, phenytoin, procainamide, and quinidine; (42) class antiarrhythmics II, such as atenolol, metoprolol, propranolol, and timolol; (43) class III antiarrhythmics, such as amiodarone; (44) class IV antiarrhythmics, such as diltiazem and verapamil; (45) antihypertensives, such as prazosin; (46) angiotensin-converting enzyme inhibitor (ACE inhibitor) antihypertensives, such as captopril and enalapril; (47) antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diuretic antihypertensive agents, such as amiloride, furosemide, hydrochlorothiazide (HCTZ), and spironolactone; (51) peripheral vasodilator antihypertensives, such as minoxidil; (52) antilipemics, such as gemfibrozil and probucol; (53) bile acid sequestrant antilipemics, such as cholestyramine; (54) reductase inhibitor antilipemics, such as lovastatin and pravastatin; (55) inotropes, such as amrinone, dobutamine, and dopamine; (56) cardiac glycoside inotropes, such as (57) thrombolytic agents, such as alteplase, anistreplase, streptokinase, and urokinase; (58) dermatological agents, such as colchicine, isotretinoin, methotrexate, minoxidil, tretinoin (59) dermatological corticosteroid anti-inflammatory agents, such as betamethasone and dexamethasone; (60) antifungal topical anti-infectives, such as amphotericin clotrimazole, miconazole, and nystatin; (61) antiviral topical anti-infectives, such as acyclovir; (62) topical antineoplastics, such as (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes and (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) H2-blocker anti-ulcer agents, such as cimetidine, famotidine, nizatidine, ranitidine; (74) digestants, such as pancrelipase; (75) prokinetic agents, such as erythromycin; (76) opiate agonist intravenous anesthetics such as fentanyl; (77) hematopoietic antianemia agents, such as (G-CSF), and (GM-CSF); (78) coagulation agents, such as factors 1-10 (AIIF 1-10); (79) anticoagulants, such as warfarin; (80) thrombolytic enzyme coagulation agents, such as alteplase, anistreplase, streptokinase and urokinase; (81) hormones and hormone modifiers, such as bromocriptine; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadotropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-lb and interferon gamma-lb; (93) immunoglobulins, such as immune globulin 1M, IMIG, IGIM and immune globulin IVIG; (94) amide local anesthetics, as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs such as diclofenac, ibuprofen, ketoprofen, ketorlac, and naproxen; (99) skeletal muscle relaxants, such as and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenytoin, and valproic acid; (103) barbiturate anticonvulsants, such as phenobarbital and primidone; (104) benzodiazepine anticonvulsants, such as clonazepam, diazepam, and lorazepam; (105) anti-agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) anti-glaucoma agents, such as timolol; (110) mitotic anti-glaucoma agents, such as pilocarpine; (111) ophthalmic aminoglycoside anti-infectives, such as gentamicin, neomycin, and tobramycin; (112) ophthalmic quinolone anti-infectives, such as ciprofloxacin, norfloxacin, and ofloxacin; (113) ophthalmic corticosteroid anti-agents, such as dexamethasone and prednisolone; (114) ophthalmic nonsteroidal anti-inflammatory drugs such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) such as codeine; (119) bronchodilators, such as (120) adrenergic agonist bronchodilators, such as albuterol; (121) respiratory corticosteroid anti-inflammatory agents, such as dexamethasone; (122) antidotes, such as flumazenil and naloxone; (123) heavy metal agents, such as penicillamine; (124) deterrent substance abuse agents, such as disulfiram, naltrexone, and nicotine; (125) withdrawal substance abuse agents, such as bromocriptine; (126) minerals, such as iron, calcium, and magnesium; (127) vitamin B compounds, such as cyanocobalamin (vitamin B12) and niacin (vitamin B3); (128) vitamin C compounds, such as ascorbic acid; and (129) vitamin D such as calcitriol.

Further, recombinant or cell-derived proteins can be used, such as recombinant beta-glucan; bovine immunoglobulin concentrate; bovine superoxide dismutase; formulation comprising fluorouracil, epinephrine, and bovine collagen; recombinant hirudin (r-Hir), HIV-1 immunogen; recombinant human growth hormone recombinant EPO (r-EPO); gene-activated EPO (GA-EPO); recombinant human hemoglobin (r-Hb); recombinant human mecasermin (r-IGF-1); recombinant interferon α; lenograstim (G-CSF); olanzapine; recombinant thyroid stimulating hormone (r-TSH); and topotecan.

Still further, the following listing of peptides, proteins, and other large molecules can also be used, such as interleukins 1 through 18, including mutants and analogues; interferons a, y, and which can be useful for cartilage regeneration, hormone releasing hormone (LHRH) and analogues, gonadotropin releasing hormone transforming growth factor (TGF); fibroblast growth factor (FGF); tumor necrosis factor-α); nerve growth factor (NGF); growth hormone releasing factor (GHRF), epidermal growth factor (EGF), connective tissue activated osteogenic factors, fibroblast growth factor homologous factor (FGFHF); hepatocyte growth factor (HGF); insulin growth factor (IGF); invasion inhibiting factor-2 (IIF-2); bone morphogenetic proteins 1-7 (BMP 1-7); somatostatin; thymosin-a-y-globulin; superoxide dismutase (SOD); and complement factors, and biologically active analogs, fragments, and derivatives of such factors, for example, growth factors.

Members of the transforming growth factor (TGF) supergene family, which are multifunctional regulatory proteins, can be incorporated in a polymer matrix. Members of the TGF supergene family include the beta transforming growth factors (for example, TGF-131, TGF-132, TGF-133); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (lGF)), (for example, lnhibin A, lnhibin B), growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

The methods, pharmaceutical compositions, and compounds disclosed herein can be combined to provide one, two or more compounds disclosed herein, optionally with, e.g., maribavir, foscarnet, GCV, and/or letermovir.

Various forms of the biologically active agents can be used. These include, without limitation, such forms as uncharged molecules, molecular complexes, salts, ethers, esters, amides, prodrug forms and the like, which are biologically activated when implanted, injected or otherwise placed into a subject.

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration and are not to be construed as limiting in any manner to make compounds of the disclosure by other methods.

EXAMPLES

Example 1

Materials and Methods

Compounds: The compounds were identified from a high throughput screen (HTS) and then validated using several HCMV strains, multiple antiviral assays and new compound preparations. In addition to compounds obtained from the libraries used in the screening, NFU1827 was synthesized in the Department of Biochemistry, Program in Chemical Biology at the Medical College of Wisconsin, MLS8091 was purchased from Princeton Biomolecular Research, Inc., MLS8969 was purchased from ChemBridge Corporation, San Diego, CA, MLS8554 was purchased from InterBioScreen STOCK1N-59867, and NCGC2955 was synthesized in the Chemistry Core, Johns Hopkins University School of Medicine. The purity of all synthesized and purchased compounds used in bioassays was determined by HPLC using either a Phenomenex Luna C18 3.0×75 mm column with a 7 min gradient of 4-100% ACN in $H_2O$ with 0.05% v/v TFA or a Higgins Analytical, Inc. Targa C18 5 μm 4.6×150 mm column with a 30 min gradient of 0-100% ACN in $H_2O$ with 0.01% TFA and either absorbance detection at 254 nm or evaporative light scattering detection. All compounds used in bioassays exhibited NMR and MS data consistent with their structures and purities of >95% as determined by HPLC.

Compounds were dissolved in dimethyl sulfoxide (DMSO), and stock solutions of 50 and 10 mM were stored at −80° C. Ganciclovir was purchased from Sigma Aldrich (St. Louis, MO), a 10 mM stock solution was prepared in $ddH_2O$.

Synthesis of NCGC2955: tert-butyl 4-(isopropylcarbamoyl) piperidine-1-carboxylate (1). To a solution of 1-(tert-butoxycarbonyl) piperidine-4-carboxylic acid[35] (3.94 g, 17.2 mmol, 1.0 equiv.) in $CH_2Cl_2$ (39 mL) was added N-(3-dimethylaminopropyl)-N'-ethylcarbodiimide hydrochloride (3.46 g, 18.0 mmol, 1.05 equiv.), 1-hydroxybenzotriazole monohydrate (2.83 g, 18.5 mmol, 1.075 equiv.) and isopropylamine (5.1 mL, 60.15 mmol, 3.5 equiv.). After stirring at room temperature for 21 h, the reaction was diluted with $CH_2Cl_2$, and washed with 5% aq. HCl. The aqueous layer was extracted with $CH_2Cl_2$ (3×20 mL). The organic layers were combined, dried with anhydrous $MgSO_4$, and concentrated in vacuo. Purification by flash chromatography (0 to 100% EtOAc/hexanes) provided 2.95 g compound 1 as a solid in 63% yield. $^1$H NMR (500 MHz, $CDCl_3$) δ 5.28 (d, J=6.45 Hz, 1H), 4.01-4.25 (m, 3H), 2.73 (br. s., 2H), 2.16 (tt, J=3.69, 11.63 Hz, 1H), 1.79 (d, J=11.32 Hz, 2H), 1.61 (dq, J=4.24, 12.42 Hz, 2H), 1.45 (s, 9H), 1.14 (d, J=6.60 Hz, 6H).

N-isopropylpiperidine-4-carboxamide trifluoroacetic acid salt (2). To a solution of compound 1 (2.95 g, 10.9 mmol) in CH2Cl2 (5 mL) was added triisopropylsilane (250 μL) and trifluoroacetic acid (3 mL) at room temperature. After stirring for 24 h at room temperature, the volatiles were removed in vacuo providing a viscous syrup used without further purification. 1H NMR (500 MHz, CDCl3) δ 4.06 (qd, J=6.86, 13.38 Hz, 1H), 3.57 (d, J=12.89 Hz, 2H), 3.10 (br. s., 2H), 2.45-2.63 (m, 1H), 2.05-2.16 (m, 4H), 1.18 (d, J=6.60 Hz, 6H).

methyl 4-(4-chlorobenzyl)-4H-thieno[3,2-b] pyrrole-5-carboxylate (3). To a suspension of methyl 4H-thieno[3,2-b] pyrrole-5-carboxylate36 (1.44 g, 7.99 mmol, 1.0 equiv.) and cesium carbonate (3.91 g, 12.0 mmol, 1.5 equiv.) in anhydrous DMF (10 mL) was added 4-chlorobenzyl bromide (1.97 g, 9.59 mmol, 1.2 equiv.) in one portion at rt. After stirring at rt until complete (ca. 4 h), the reaction was diluted with water and extracted with EtOAc (3×20 mL). The organic layers were combined, washed with brine, dried with anhydrous MgSO4, and concentrated in vacuo. Purification by flash chromatography (3 m 0%, 6 m gradient 0 to 50%, 2 m 50% EtOAc/hexanes) provided 2.40 g of methyl ester 3 as a pale yellow solid in 98% yield. 1H NMR (500 MHz, CDCl3) δ 7.33 (d, J=5.34 Hz, 1H), 7.21-7.29 (m, 3H), 7.05 (d, J=8.17 Hz, 2H), 6.85 (d, J=5.50 Hz, 1H), 5.71 (s, 2H), 3.83 (s, 3H).

4-(4-chlorobenzyl)-4H-thieno[3,2-b] pyrrole-5-carboxylic acid (4). To a mixture of methyl ester 3 (3.58 g, 11.7 mmol, 1.0 equiv.) in THE (12 mL) and MeOH (12 mL) was added a solution of lithium hydroxide monohydrate in water (12 mL) in one portion. After 2 d of rapid magnetic stirring at rt, the starting material was consumed, and the organic solvents were removed in vacuo. The remaining aqueous solution was diluted with water (ca. 20 mL) and under vigorous magnetic stirring the pH was adjusted to pH=1 with conc. aq. HCl. A precipitate formed during acidification, and was collected via vacuum filtration, washed with water and dried under vacuum to provide 3.34 g of compound 4 in 98% yield. 1H NMR (500 MHz, DMSO-d6) δ 12.57 (br. s., 1H), 7.56 (d, J 5.19 Hz, 1H), 7.29-7.43 (m, J 8.49 Hz, 2H), 7.17-7.29 (m, 2H), 7.05-7.17 (m, J 8.49 Hz, 2H), 5.76 (s, 2H).

1-(4-(4-chlorobenzyl)-4H-thieno[3,2-b] pyrrole-5-carbonyl)-N-isopropylpiperidine-4-carboxamide (NCGC2955). To a mixture of compound 4 (51.9 mg, 0.177 mmol, 1.0 equiv.) in $CH_2Cl_2$ (1.7 mL) was added N-(3- dimethylaminopropyl)-N'-ethylcarbodiimide hydrochloride (37.5 mg, 0.19 mmol, 1.1 equiv.), 1-hydroxybenzotriazole monohydrate (31.0 mg, 0.204 mmol, 1.15 equiv.) and diisopropylethylamine (123 μL, 0.71 mmol, 4 equiv.). After stirring at room temperature for 5 min, TFA salt 2 (60.7 mg, 0.21 mmol, 1.2 equiv.) was added as a solution in $CH_2Cl_2$ (0.2 mL, plus 0.2 mL rinse) and the reaction stirred at rt. After 24 h, the reaction was diluted with $CH_2Cl_2$, and washed with 5% aq. HCl. The aqueous layer was extracted with EtOAc (3×10 mL). The organic layers were combined, dried with anhydrous $MgSO_4$, and concentrated in vacuo. Purification by flash chromatography (0 to 100% EtOAc/hexanes) provided 48.9 mg of NCGC2955 as a white solid in 62% yield. $^1$H NMR (500 MHz, $CDCl_3$) δ 7.24 (d, J=8.33 Hz, 2H), 7.18 (d, J=5.19 Hz, 1H), 7.08 (d, J=8.33 Hz, 2H), 6.83 (d, J=5.19 Hz, 1H), 6.58 (s, 1H), 5.43 (s, 2H), 5.19 (d, J=8.02 Hz, 1H), 4.44 (d, J=12.89 Hz, 2H), 4.08 (qd, J=6.77, 13.34 Hz, 1H), 2.92 (t, J=12.34 Hz, 2H), 2.24 (tt, J=3.62, 11.08 Hz, 1H), 1.80 (d, J=14.93 Hz, 2H), 1.43-1.63 (m, 6H), 1.15 (d, J=6.60 Hz, 6H).

Synthesis of NFU1827: 4-(4-methoxyphenyl)-7-thia-2,5-diazatricyclo [6.4.0.02,6]dodeca-1(8),3,5,9,11-pentaene-10-carboxylic acid (5). 2-Aminobenzothiazole-6-carboxylic acid (2.0 g, 10.30 mmol, 1.0 equiv.) and 2-bromo-4'-methoxyacetophenone (2.60 g, 11.33 mmol, 1.1 equiv.) were charged to a pressure bottle and suspended in 2-methoxyethanol (50 mL). The suspension was heated to 40° C. for 24 h and at 140° C. for 19 h. The reaction was allowed to cool to rt and concentrated in vacuo. The crude compound was purified by flash column chromatography (5 to 75% EtOAc/hexanes) to afford 1.83 g of compound 6 in 55% yield. $^1$H NMR (500 MHz, DMSO-$d_6$) δ 13.17 (broad s, 1H), 8.69 (s, 1H), 8.63 (d, J=1.2 Hz, 1H), 8.10 (dd, J=1.6, 8.3 Hz, 1H), 8.01 (d, J=8.4 Hz, 1H), 7.78 (d, J=8.7 Hz, 1H), 6.99 (d, J=8.8 Hz, 1H), 3.77 (s, 3H).

N-[3-(4-ethylpiperazin-1-yl)propyl]-4-(4-methoxyphenyl)-7-thia-2,5-diazatricyclo [6.4.0.02,6] dodeca-1(8),3,5,9,11-pentaene-10-carboxamide (NFU1827). Compound 5 (100 mg, 0.308 mmol), N-(3-Dimethylaminopropyl)-N'-ethylcarbodiimide hydrochloride (118.2 mg, 0.617 mmol), and 1-hydroxybenzotriazole hydrate (83.3 mg, 0.617 mmol) were dissolved in DMF and stirred at room temperature for 1 h. The reaction was then treated with 3-(4-ethylpiperazin-1-yl) propan-1-amine (0.2269 mL, 211.2 mg, 1.23 mmol) and stirred at room temperature for 18 h. The reaction was then poured into $H_2O$ (20 mL). This was extracted with EtOAc (3×20 mL). The combined extracts were washed with $H_2O$ (4×20 mL) followed by brine (1×20 mL). The organic layer was dried ($Na_2SO_4$), filtered, and the solvent removed in vacuo. The crude compound was purified by flash column chromatography using hexanes/EtOAc (gradient elution from 90:10 to 0:100) to afford 60 mg of NFU1827 in 41% yield. 1H NMR (500 MHz, CDCl3) δ 8.71 (s, 1H), 8.21 (s, 1H), 7.99 (d, J=8.4 Hz, 1H), 7.91 (s, 1H), 7.80 (d, J=8.7 Hz, 2H), 7.62 (d, J=8.4 Hz, 1H), 6.96 (d, J=8.7 Hz, 2H), 3.85 (s, 3H), 3.60 (q, J=5.2 Hz, 2H), 2.63 (t, J=5.5 Hz, 2H), 2.46 (q, J=7.3 Hz, 2H), 1.82 (m, 2H), 1.78 (broad s, 8H), 1.10 (t, J=7.2 Hz, 3H). 13C NMR (126 MHz, CDCl3) δ 162.72, 156.34, 145.14, 130.89, 128.49, 127.24, 123.49, 123.25, 122.78, 120.26, 111.13, 109.09, 102.92, 57.32, 55.69, 52.27, 50.25, 49.91, 49.39, 38.42, 26.62, 20.55, 17.98, 11.12. HRMS (ESI$^+$) m/z calcd for $C_{26}H_{31}N_5O_2S$ $[M+H]^+$ 478.2272, found 478.2271.

Cells: Human Foreskin fibroblasts (HFFs), passage 12 to 16; (ATCC, CRL-2088) were grown in Dulbecco's modified Eagle medium (DMEM) containing 10% fetal bovine serum (FBS) (Gibco, Carlsbad, CA) in a 5% $CO_2$ incubator at 37° C. Mouse embryonic fibroblasts (MEFs, ATCC, CRL-1658) were used for infection with mouse CMV. Vero cells were obtained from the laboratory of Dr. Gary Hayward, Johns Hopkins University School of Medicine.

Cytotoxicity assay: MTT assay was performed as described by manufacturer's instructions (Sigma-Aldrich). Non-infected cells were treated with compounds for 72 h or 10 days (same time points of the antiviral assay), and 20 μL/well of MTT [3-(4, 5-Dimethyl-2-thiazolyl)-2, 5-diphenyl-2H-tetrazolium bromide], 5 mg/mL in phosphate buffered saline (PBS)] was added to each well. After shaking at 150 rpm for 5 min the plates were incubated at 37° C. for 2-3 h. Conversion of yellow solution to dark blue formazan by mitochondrial dehydrogenases of living cells was quantified by measuring absorbance at 560 nm.

Viruses and antiviral assays: A recombinant pp28-luciferase Towne HCMV strain expressing luciferase under the control of the UL99 (pp28) late promoter was reported to provide a highly-sensitive and reproducible reporter for drug screening[20]. A GCV-resistant HCMV pp28-luciferase that contains a C607Y mutation in UL97 was reported[37]. The HCMV TB40 strain was obtained from ATCC (VR-1578). Clinical isolates of Human Herpesvirus 1 and 2 (HSV1, HSV2) were collected from the Johns Hopkins Microbiology laboratory without identifiers that could link them to a specific patient. Mouse CMV (MCMV) Smith strain (ATCC VR-1399) was used for infection of MEFs.

Luciferase activity: Cell lysates were collected at 72 hpi and luciferase activity was determined using the Glomax-Multi+Detection System (Promega, Madison, WI) as described previously[20].

Plaque reduction assay: HFFs were seeded into 12-well plates ($2\times10^5$ cells/well) and infected with HCMV TB40 at approximately 100 plaques/well. After 90 min, media were aspirated, and DMEM containing 0.5% carboxymethylcellulose (CMC), 4% fetal bovine serum (FBS), and drugs were added into duplicate wells. Following incubation at 37° C. for 10-12 days the overlay was removed, and plaques were counted after crystal violet staining. For HSV1 and HSV2 replication in Vero cells, the adsorption time was 60 min and plaques were counted after 36 h. Plaque assays in MEFs were completed after 3 days.

Inhibition of lytic Epstein Barr Virus (EBV) replication: Akata cells ($0.5\times10^6$/well of 24-well plate) latently infected with EBV were induced with 100 μg/ml of goat antihuman IgG (Sigma). Compounds and GCV control were added to triplicate wells immediately after the addition of human IgG. Cells were collected 48 hours after lytic induction for DNA quantification. Cellular DNA was purified using Wizard SV Genomic Kit (Promega, Madison, WI). The effect of the compounds on lytic induction of EBV was analyzed by real-time PCR of the EBV DNA polymerase gene, BALF5[38].

Add-on and removal assays: These assays were performed to identify at which stage during HCMV replication the compounds had maximal activity. In the add-on group, compounds were added to infected HFFs at 0, 6, 24, and 48 hpi, and luciferase activity was measured at 72 hpi. In the removal group, compounds were added immediately after virus infection and were subsequently removed after 0, 6, 24, and 48 h; luciferase was measured at 72 hpi.

DNA isolation and quantitative real-time (qPCR): Total DNA was isolated from non-infected control, and HCMV-infected HFFs using Wizard SV genomic DNA isolation kit (Promega, Madison, WI). To determine viral load in the supernatant, total DNA was isolated from supernatants using automated DNA extraction on the BioRobot M48 instrument (Qiagen, Valencia, CA). A US17 real-time PCR assay which targets 151-bp from the highly conserved US17 region of the CMV genome was used[39]. The primers and probe for US17 are:

```
forward
                                  (SEQ ID NO: 1)
5'-GCGTGCTTTTTAGCCTCTGCA-3',

reverse
                                  (SEQ ID NO: 2)
5'-AAAAGTTTGTGCCCCAACGGTA-3',
and

US17 probe FAM
                                  (SEQ ID NO: 3)
5'-TGATCGGGCGTTATCGCGTTCT-3'.
```

HCMV entry and indirect immunofluorescence assay: MLS8969, GCV and heparin control were used to determine inhibition of HCMV entry. Compounds were diluted in serum-free media and added to HFFs seeded on chamber slides 24 h prior to infection. After infection (MOI 1 or 0.1 PFU/cell) for 2 h, cells were fixed with 100% chilled methanol, blocked for 1 h with phosphate-buffered saline (PBS), 5% serum, 0.3% Triton X-100. Cells were then incubated with mouse monoclonal anti-pp65 antibody, 1:50 (Vector Laboratories, Burlingame, CA) at 37° C. in humidified chambers for 1 h, washed three times with TBST (0.1%), incubated with rhodamine-conjugated anti-mouse IgG, 1:500 (Sigma) at 37° C. in humidified chambers for 1 h and washed with TBST (0.1%). A drop of mount oil containing DAPI (Santa Cruz Biotechnology, Santa Cruz, CA) was added to the slides before visualization with a Zeiss ZI fluorescence microscope. Images were captured at 40× magnification.

SDS-polyacrylamide gel electrophoresis and immunoblot analysis: Cell lysates containing equal amount of proteins were mixed with an equal volume of sample buffer (125 mM Tris-HCL, pH 6.8, 4% SDS, 20% glycerol and 5% β-mercaptoethanol) and boiled at 100° C. for 10 min. Denatured proteins were resolved in Tris-glycine polyacrylamide gels (8-10%) and transferred to polyvinylidine difluoride (PVDF) membranes (Bio-Rad Laboratories, Hercules, CA) by electroblotting. Membranes were incubated in blocking solution [5% w/v non-fat dry milk and 0.1% Tween-20 in PBS (PBST)] for 1 h, washed with PBST, and incubated with primary antibodies at 4° C. overnight. Membranes were washed with PBST and incubated with horseradish peroxidase-conjugated secondary antibodies in PBST for 1 h at room temperature. Following washing with PBST, protein bands were visualized by chemiluminescence using SuperSignal West Dura and Pico reagents (Pierce Chemical, Rockford, IL).

Antibodies: The following antibodies were used—Mouse monoclonal anti-HCMV IE1 & IE2 (MAB810, Millipore, Billerica, MA), mouse monoclonal anti-HCMV UL83 (pp65, Vector Laboratories Inc., Burlingame, CA), mouse monoclonal anti-HCMV UL44, mouse monoclonal anti-HCMV UL84, and mouse anti-β-actin anti-mouse IgG (Santa Cruz Biotechnology, Santa Cruz, CA). Horseradish peroxidase (HRP)-conjugated anti-mouse IgG was from GE Healthcare (Waukesha, WI). Horseradish peroxidase (RP)-conjugated anti-rabbit IgG was from Cell Signaling (Beverly, MA).

Drug combination and analysis: These experiments were performed as previously reported[40]. The combination of GCV and each compound was tested using the pp28-luciferase. Briefly, $2\times10^6$ HFFs/plate were seeded in 96-well plates and infected with the pp28-luciferase Towne HCMV strain (MOI=1). First, a dose response curve was generated for each drug individually to determine its $EC_{50}$. Then, drugs were combined at twice their $EC_{50}$, diluted in DMEM with 4% FBS, followed by serial dilution and added together after infection. Luciferase activity of the combination and each drug individually was quantified at 72 hpi. The combination of letermovir and each of the new compounds was tested by the plaque assay using TB40. The same principle applied in this assay for the drug combination effect, and plaques were counted at 8 dpi. The Bliss model was used to calculate the effect of each drug combination on pp28-luciferase activity and plaque reduction. In this model, drug combination represents the product of two probabilistically independent events as described in the following equation[41].

$$F_{U1+2} = F_{U1} \cdot F_{U2} = \frac{1}{1 + \left(\frac{D_1}{EC_{50(1)}}\right)^{m_1}} \cdot \frac{1}{1 + \left(\frac{D_2}{EC_{50(2)}}\right)^{m_2}}$$

Where D is the drug concentration, m is the slope, and $EC_{50}$ is the effective concentration resulting in 50% virus inhibition. The combined effect of two inhibitors (Fu, fractional unaffected) is computed as the product of individual effects of the two inhibitors, $Fu_1$ and $Fu_2$. If the ratio of observed fold inhibition divided by the expected fold inhibition is greater than 1, the compounds are synergistic. If the ratio is less than 1, the combination is considered antagonistic, and if it equals to 1 the combination is additive.

Statistical analysis: A student t-test was performed using Sigmaplot (Systat Software, San Jose, CA) and GraphPad Prism (GraphPad Software, La Jolla, CA). All sample groups were compared to the control group using a One-way ANOVA. P-values were adjusted for multiple comparisons. In all the figures, the following convention has been followed. * indicates p value <0.05,  indicates p<0.01, and * indicates p<0.001. The curve fitting toolbox, MATLAB software (v7.10), MathWorks (Natick, MA) was used to determine $EC_{50}$ and $CC_{50}$ values using a four-parameter logistic regression.

Example 2

High throughput screening for HCMV inhibitors: The pp28-HCMV luciferase, which has been shown to provide highly reproducible and sensitive results for HCMV inhibition with compounds, was used for screening of the MLSMR collection of 370,000 compounds, the NCGC diversity collection of 65,000 compounds and the NCGC Pharmaceutical Collection of approved and investigational drugs. The screening used 2 compound doses plated before infection and lysates were tested for luciferase activity at 72 hours post infection (hpi). A total of 2215 inhibitors of HCMV-luciferase were selected using published compound dose response curve algorithms[21]. A secondary screen was performed to remove compounds that showed toxicity in human foreskin fibroblasts (HFFs) resulting in 847 confirmed, non-toxic HCMV inhibitors (FIG. 1).

HCMV inhibition was measured by luciferase activity of pp28-recombinant Towne and pp28 GCV-resistant Towne strains of HCMV (72 hpi) and by plaque reduction using HCMV Towne or TB40 (10 days). Viral protein expression was measured by Western blot. A colorimetric MTT assay was performed in non-infected HFFs to determine cell cytotoxicity in parallel to the infectivity assay, i.e. at 72 h and at 10 days and is represented as CC50. All 5 compounds were active at sub to low µM concentrations against all the HCMV strains used. Based on plaque reduction, MLS8969 had the best activity against HCMV followed by MLS8091, MLS8554, NCGC2955 and NFU1827 (Table 1).

TABLE 1

Anti-HCMV activity of the 5 compounds against different strains of HCMV, toxicity and slope

| Compound | $EC_{50}$—Towne (µM) | $EC_{50}$—GCVR Towne (µM) | $EC_{50}$—TB40 (µM) | $CC_{50}$ (µM) | Slope |
|---|---|---|---|---|---|
| MLS8969 | 0.55 ± 0.1* | 0.25 ± 0.1* | 0.12 ± 0.0* | >500 | 0.64 ± 0.06* |
| NFU1827 | 0.85 ± 0.1 | 0.84 ± 0.1 | 1.21 ± 0.1 | 70.9 | 1.27 ± 0.1 |
| MLS8554 | 0.64 ± 0.1 | 0.17 ± 0.0 | 0.34 ± 0.0 | 86.0 | 1.02 ± 0.1 |
| MLS8091 | 0.39 ± 0.0 | 0.26 ± 0.0 | 0.33 ± 0.0 | >250 | 1.34 ± 0.1 |
| NCGC2955 | 4.61 ± 1.4 | 1.4 ± 0.2** | 1.18 ± 0.2 | >200 | 0.80 ± 0.1 |
| GCV | 2.1 ± 0.3 | 29.7 ± 1.2 | 0.72 ± 0.0 | >200 | 0.93 ± 0.1 |

* = Pre-treatment followed by plaque reduction assay
** = Plaque reduction assay The slope parameter (analogous to the Hill coefficient) was calculated for each compound. A slope of 1 represents either one binding site or non-cooperativity. A positive cooperativity exists when binding at one site increases the affinity for ligand binding at another site (slope>1). If binding at one site lowers the affinity for ligand at another site, the compound exhibits negative cooperativity (slope <1). For other chronic viral infections, such as HIV, the slope was found to be an important factor not only in distinguishing between drug classes with a known mechanism of action, but also contributing to reduced antiviral activity even when the EC50 was unchanged in resistant virus mutants 22, 23. Based on plaque reduction assays all compounds except for MLS8969 had a slope of 1.

Example 3

Inhibition of other herpesviruses: Inhibition of herpes simplex 1 and 2 (HSV1, HSV2), Epstein Barr virus (EBV) and mouse CMV (MCMV) was tested with the five compounds. Plaque reductions assays were used for HSV1, HSV2 and MCMV. Inhibition of lytic EBV replication was measured by real-time PCR in AKATA cells following IgG induction. Only MLS8554 was active against HSV1, HSV2 and MCMV (Table 2).

TABLE 2

| Activity of the five compounds against other herpes viruses; NA—Not active; CI—Clinical isolate | | | | |
|---|---|---|---|---|
| Compound | $EC_{50}$—HSV1-C1 (μM) | $EC_{50}$—HSV2-C1 (μM) | $EC_{50}$—EBV (μM) | $EC_{50}$—MCMV (μM) |
| MLS8969 | NA | NA | >10 | NA |
| NFU1827 | NA | NA | 1.92 ± 0.1 | NA |
| MLS8554 | 1.78 ± 0.2 | 1.3 ± 0.1 | NA | 11.67 ± 2.0 |
| MLS8091 | NA | NA | >10 | NA |
| NCGC2955 | NA | NA | NA | 1.0 ± 0.0 |
| GCV | 0.04 ± 0.0 | 0.58 ± 0.0 | 5.2 ± 0.4 | 0.96 ± 0.1 |

NCGC2955 was active against MCMV ($EC_{50}$ of 1 μM, table 2), but toxicity to MEFs was observed at 10 μM and higher concentrations. NFU1827 showed activity against EBV (EC50—1.92±0.1 μM). The other compounds had specific activity against HCMV and did not inhibit HSV1 or MCMV.

Example 4

Timing of HCMV inhibition: Add-on and removal assays were performed. Compounds were added or removed at 0, 6, 12, 24, 36 and 48 hpi, and luciferase activity was measured at 72 hpi. Based on these assays each compound had a specific time of maximal activity and are reported below based on timing of maximal virus suppression.

Example 5

Figure 3:
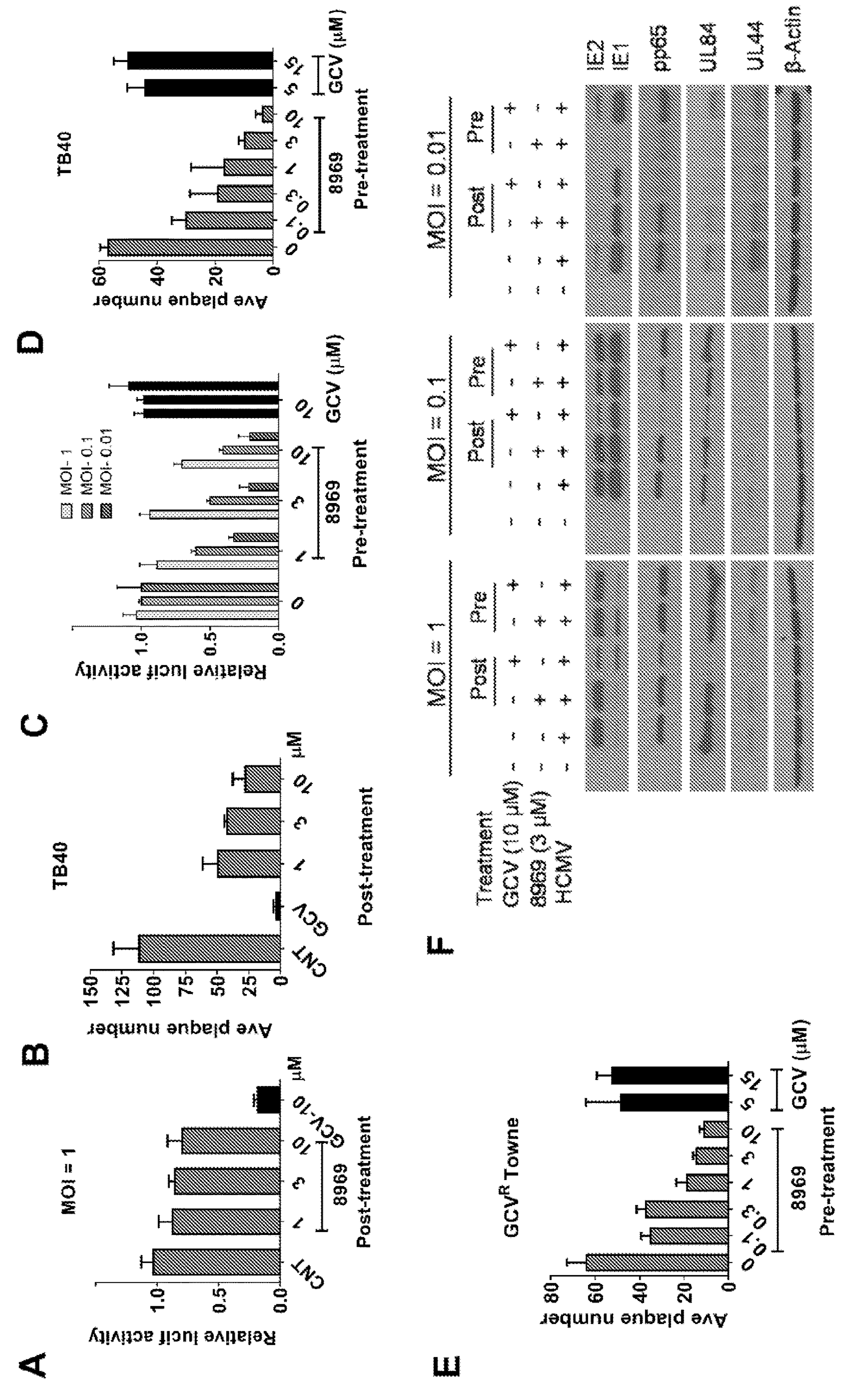
FIG. 3. MLS8969 inhibits HCMV replication FIG. 3A, HFFs were infected with HCMV Towne pp28 (MOI=1) followed by treatment with MLS8969 or GCV. At 72 hpi luciferase activity was measured.

Inhibition of HCMV entry: Compound MLS8969 was first tested after infection at MOI of 1 PFU/cell using a luciferase assay at 72 hpi, but minimal reduction in luciferase activity was observed (FIG. 3A). However, a plaque assay showed good anti-HCMV activity of MLS8969 (FIG. 3B).

Figure 4:
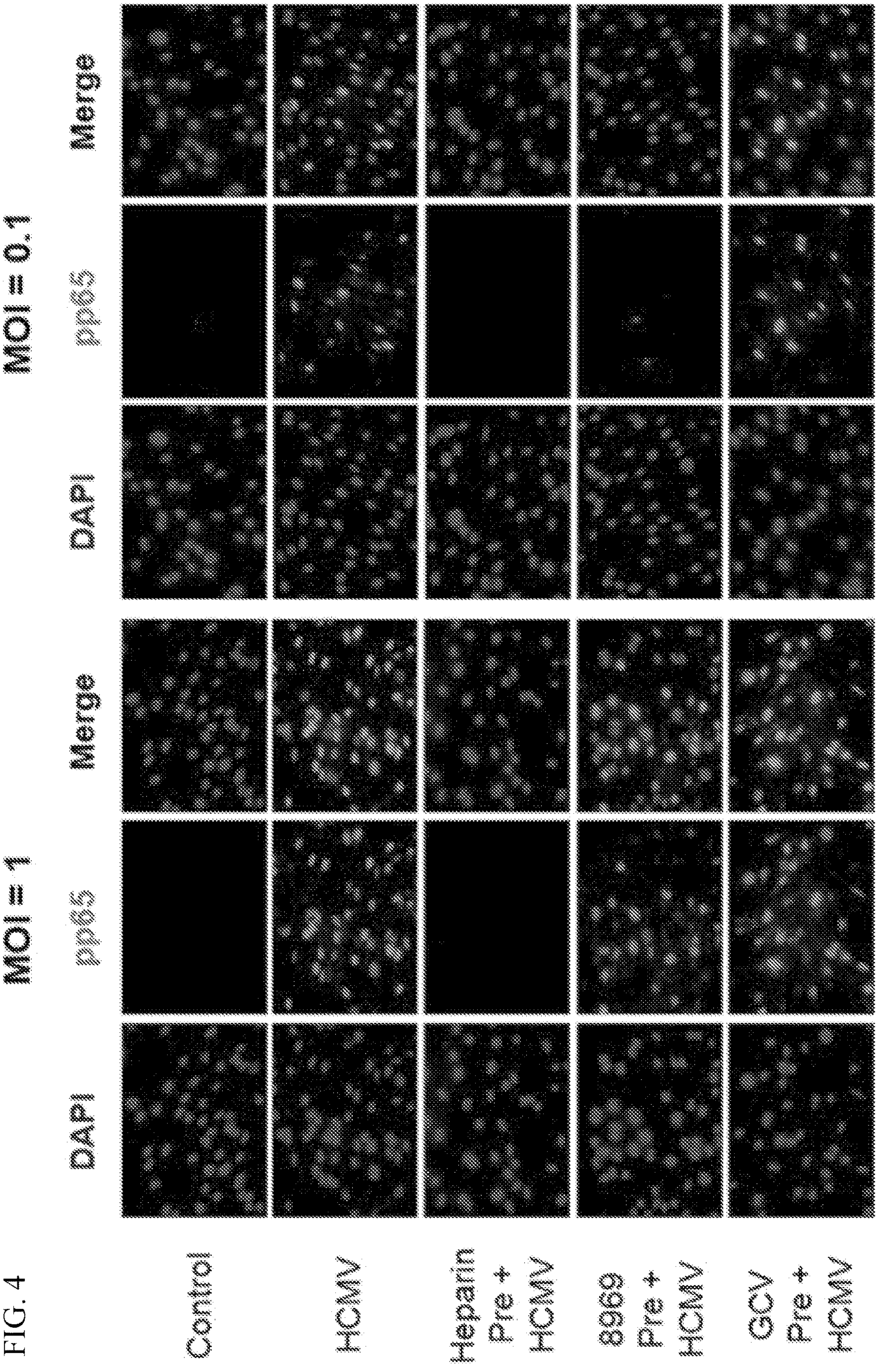
FIG. 4. MLS8969 is an entry inhibitor of HCMV. HFFs were pretreated with 3 μM MLS8969 for 24 h, followed by infection with HCMV Towne (MOI=1, 0.1, 0.01). Heparin (30 μM) was used as a positive control for blocking viral entry into the cells and GCV pretreatment (5 μM) was used as a negative control. IFA for HCMV-encoded pp65 was performed 2 hpi to determine the amount of pp65 localized in the nucleus under the different conditions. Experiment was repeated independently three times, images from a representative experiment are shown.

Because in the high-throughput screens HFFs were treated with compounds before infection (pre-treatment), and our plaque assay, in which MLS8969 was added after infection, revealed an $EC_{50}$ of 0.12±0.02 μM (Table 1), we suspected lack of inhibition of luciferase activity could represent a MOI-dependent phenomenon, and thus suggestive of entry inhibition[24]. The assay was therefore performed using MOIs of 0.01, 0.1 and 1 PFU/cell (FIG. 3C) and MLS8969 was added before infection. MOI-dependent inhibition of luciferase activity was observed (FIG. 3C). TB40 and a GCV-resistant HCMV Towne were also inhibited with MLS8969 pretreatment in plaque reduction assay (FIG. 3D, E). Western blot analysis corroborated these data, showing no inhibition of viral protein expression at post or pretreatment at MOI of 1 PFU/cell, while pretreatment followed by infection at low MOI (0.01) resulted in decreased IE1/2, pp65, UL84 and UL44 protein levels (FIG. 3F). Further evidence for MLS8969 being an entry inhibitor was obtained by an indirect immunofluorescence assay (IFA) for HCMV pp65 (FIG. 4). MLS8969 inhibited HCMV entry only at MOI of 0.1; irrespective of MOI, GCV did not affect pp65 nuclear staining (FIG. 4). Heparin (positive control) inhibited HCMV entry.

Example 6

Figure 5:
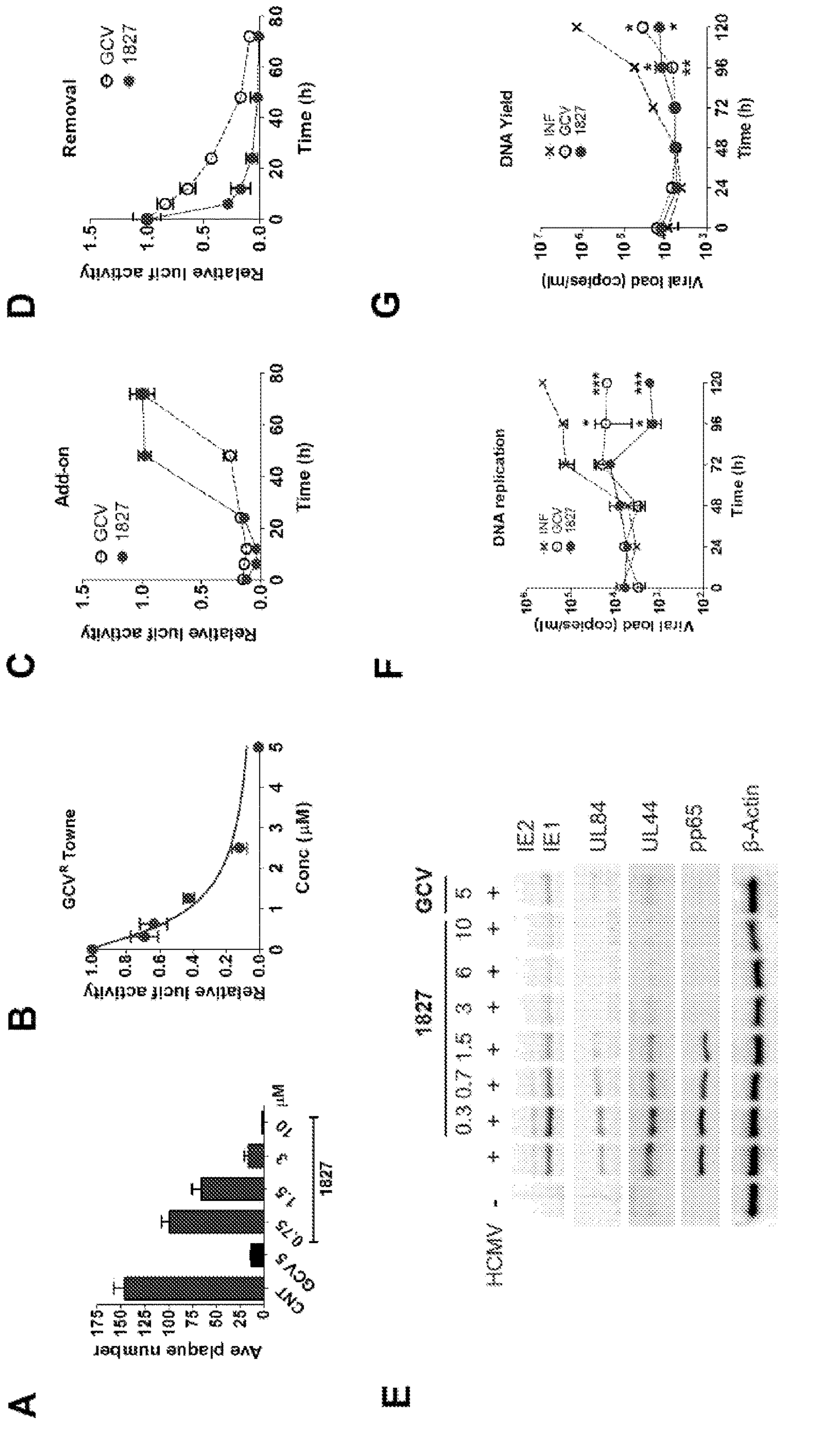
FIG. 5. NFU1827 is an immediate early-early inhibitor of HCMV replication.

Inhibitors at the immediate early-to early stage of HCMV replication: Two compounds showed anti-HCMV activity between 0-24 hpi (NFU1827 and MLS8554). NFU1827 was only active against HCMV and GCV-R HCMV, $EC_{50}$ 0.85±0.1 and 0.84±0.1 μM, respectively (Table 1, FIGS. 5 A&B) but had no activity against MCMV or HSV1 (Table 2). Add on and removal assays revealed an immediate early-early time of activity. When added to infected cells after 24 h it lost its ability to inhibit HCMV. Removal of NFU1827 after 6 h already achieved significant HCMV suppression (FIGS. 5 C&D). NFU1827 reduced the level of both IE1 and IE2 (FIG. 5E). In accordance with its immediate-early-early activity, viral DNA replication and DNA yield in supernatant was significantly reduced (FIGS. 5 F&G).

Figure 6:
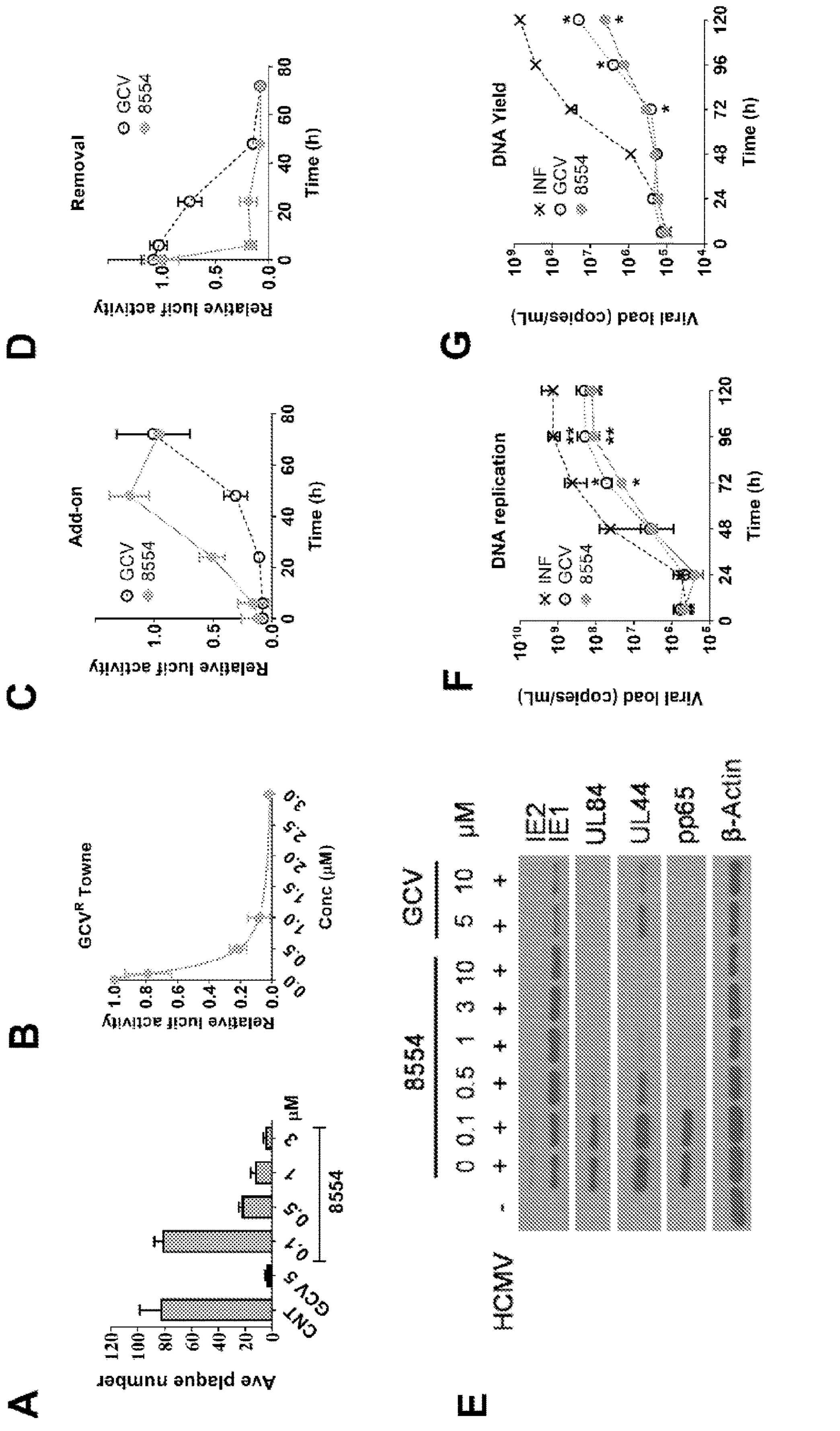
FIG. 6. MLS8554 is an immediate early-early inhibitor of HCMV replication.

MLS8554 was active in all antiviral assays inhibiting HCMV, GCV-R HCMV, MCMV and HSV1 (FIG. 6, Table 1&2). Its maximal activity was measured at immediate early-early time after infection. When added at 24 hpi or after, its activity was significantly reduced, and when removed at 6 h HCMV suppression was already near complete (FIGS. 6 C&D). Western blot at 72 hpi showed reduced expression of IE2, UL44, UL84 and pp65 (FIG. 6 E). In contrast to NFU1827 which reduced both IE1 and IE2, MLS8554 mostly reduced IE2 expression. Both viral DNA replication and DNA supernatant yield were reduced (FIGS. 6 F&G).

Example 7

Figure 7:
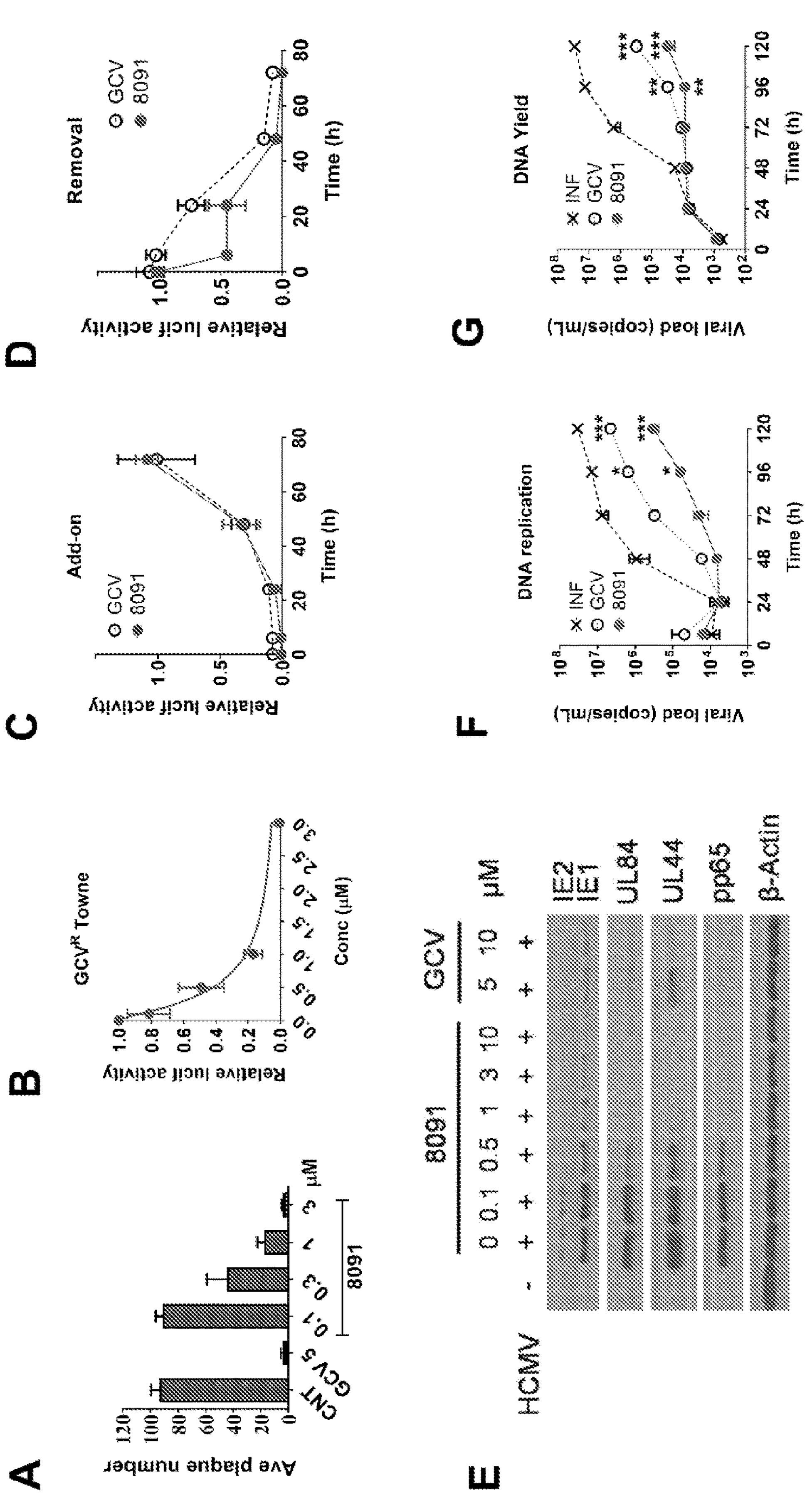
FIG. 7. MLS8091 inhibits HCMV replication at early-late stage.

Inhibitors at the early-to late stage of HCMV replication: MLS8091 showed a dose response against HCMV as well as GCV-resistant HCMV with an $EC_{50}$ of 0.39±0.0.5 and 0.26±0.02 μM, respectively (Table 1, FIG. 7), but had no activity against HSV1 or MCMV (Table 2). In the add-on assay its time of activity overlapped with that of GCV, but in the removal assay MLS8091 showed earlier effects (FIGS. 7 C&D). Inhibition of all viral proteins was observed at 72 hpi (FIG. 7E). Inhibition of viral DNA replication was higher than that achieved with GCV, although the effects on DNA yield were not significantly different from GCV (FIGS. 7 F&G).

Figure 8:
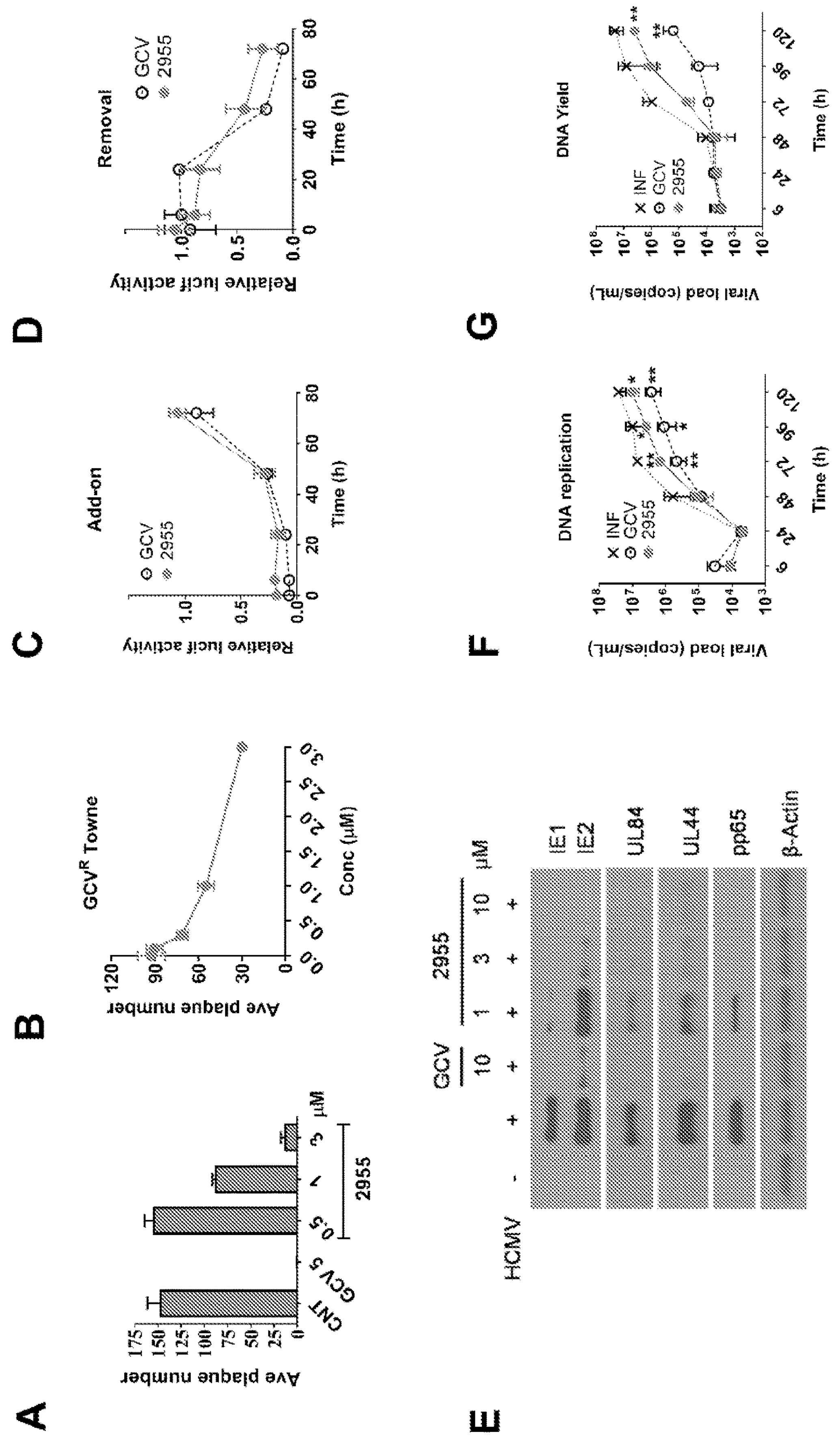
FIG. 8. NCGC2955 is an early-late inhibitor of HCMV replication.

NCGC2955 inhibited HCMV and GCV-R HCMV (FIGS. 8 A&B). For this compound plaque assays were preferred since it did not show a full dose response with the luciferase assay. In the add-on assay the timing of activity of NCGC2955 overlapped with GCV, but in the removal assay NCGC2955 appeared to have longer activity than GCV (FIGS. 8 C&D). At 72 hpi there was a strong reduction in viral protein expression including IE1 and IE2 (FIG. 8E). Despite inhibition of viral progeny by plaque assays and inhibition of viral protein expression, the effect of NCGC2955 on viral DNA replication and viral DNA yield was modest (FIGS. 8 F&G), suggesting inhibition via mechanisms that do not involve the DNA replication machinery.

Example 8

Figure 9:
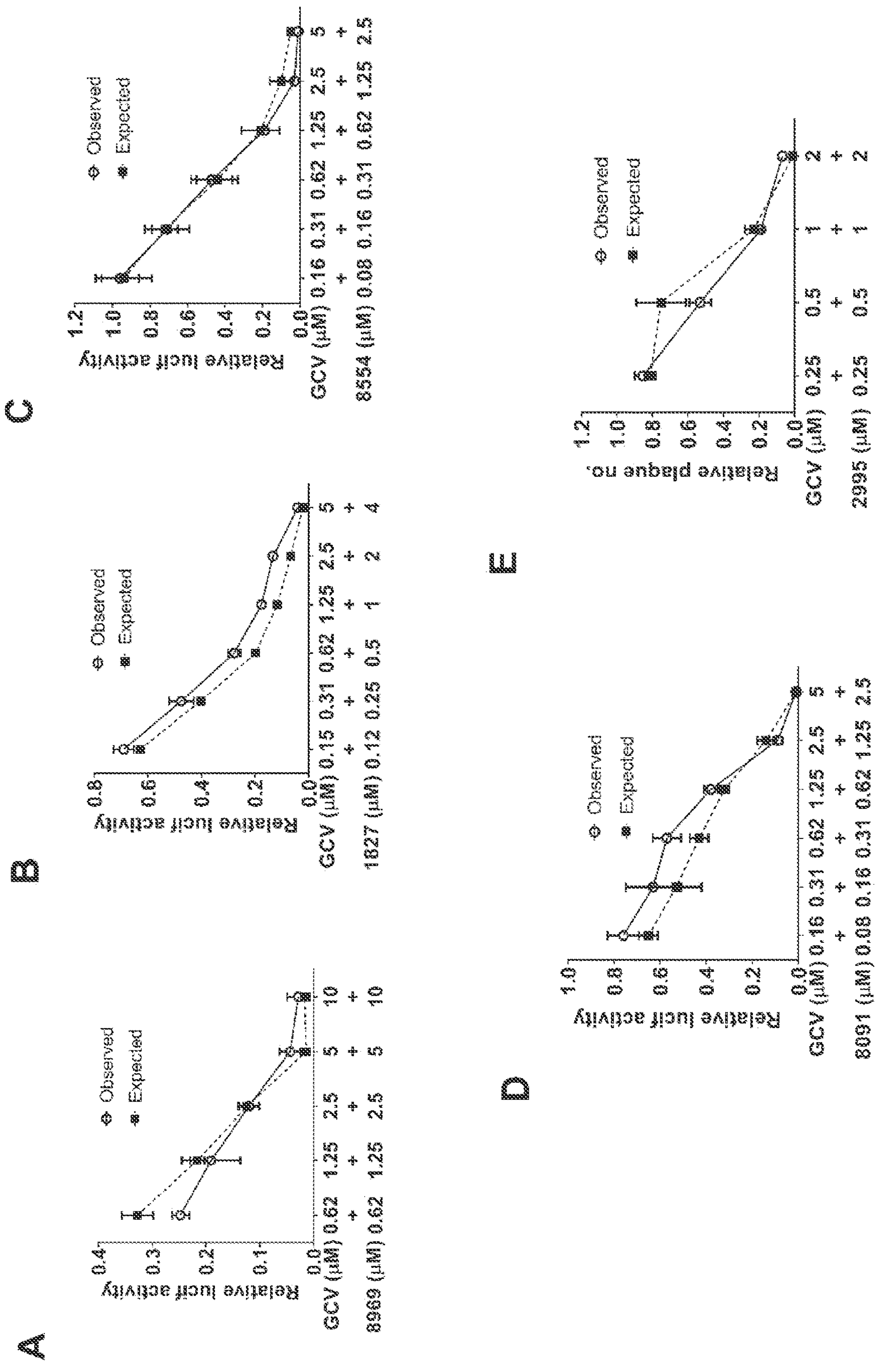
FIG. 9. Combination of newly identified HCMV inhibitors and GCV is additive.
Figure 10:
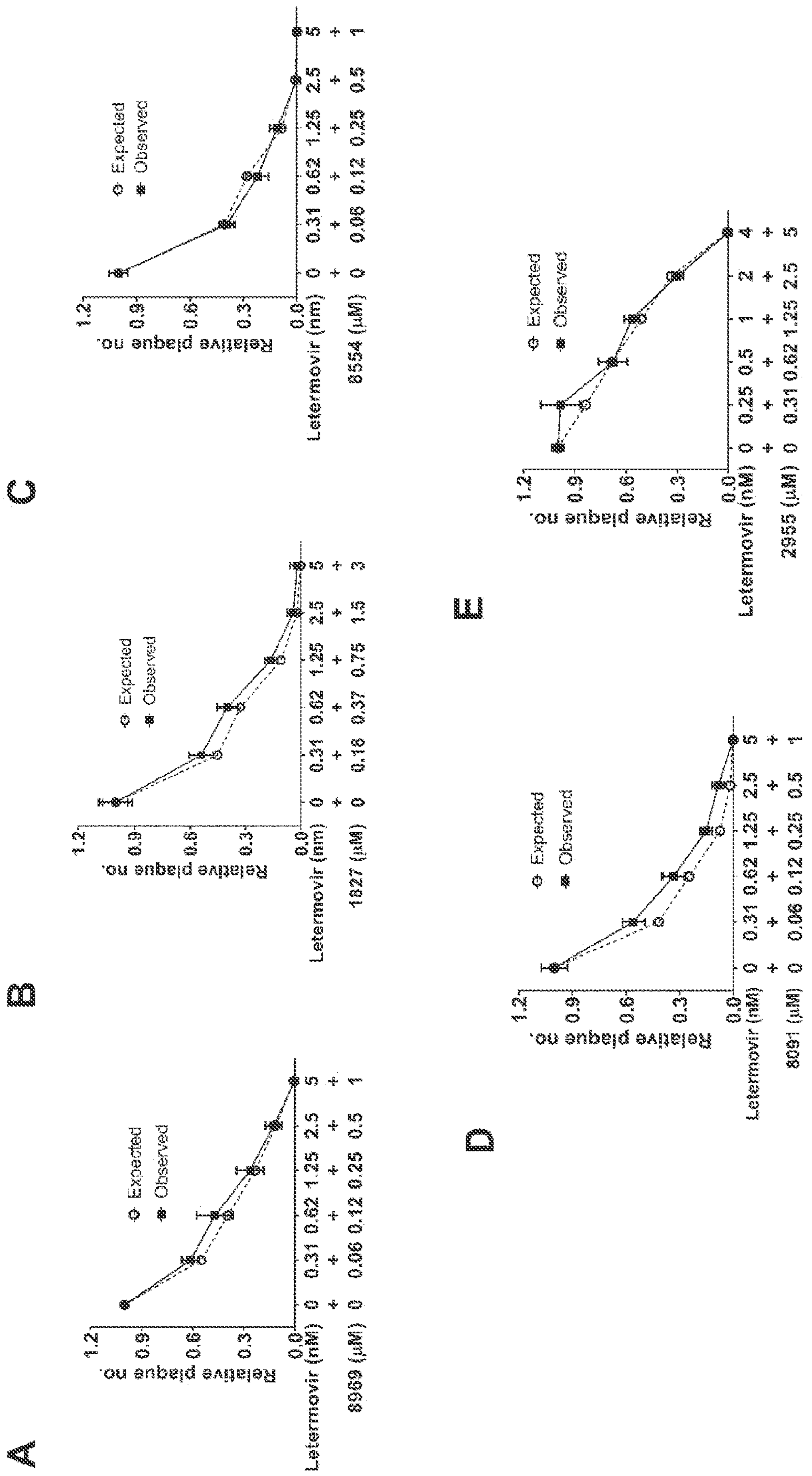
FIG. 10. Combination of newly identified HCMV inhibitors with HCMV terminase inhibitor, Letermovir is additive.
Figure 11:
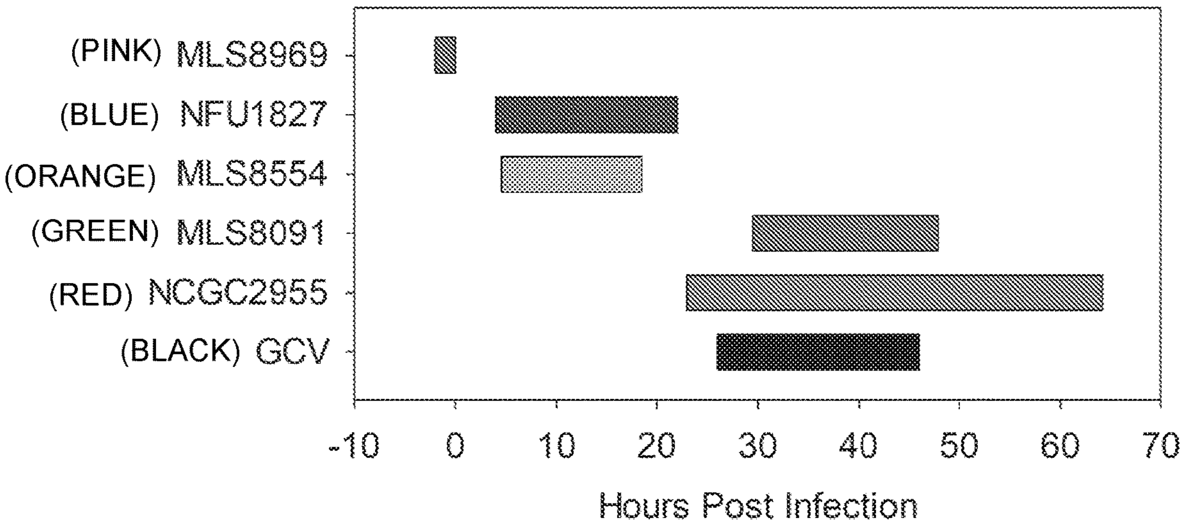
FIG. 11. Table of Contents Graphics: Time of maximal activity of the five new inhibitors and GCV during HCMV replication. Addon and removal assays were performed for each of the five compounds as described in the materials and methods section and shown for each compound in FIGS. 5-8 C&D. The timing of 75% reduction in luciferase activity was calculated for each compound both when added and when removed and is depicted in a unique color. The individual addon and removal assays are provided in FIGS. 5, 6, 7, 8C and 8D.

Pattern of drug combination with GCV and letermovir: The effect of each compound alone or in combination with GCV or letermovir was tested in HCMV-infected HFFs. An additive or mild synergistic effect was observed with GCV (FIG. 9) or letermovir (FIG. 10) for all five agents. A ratio of observed fold inhibition divided by the expected fold inhibition of >1 was considered drug synergy, <1 as drug antagonism, and =1 as additive. The Bliss coefficient of drug combination is provided in Table 3. For letermovir and its combination with each of the five compounds the $EC_{50}$ was determined based on plaque assay. The combination of GCV and 2955 was also tested by plaque assay. All other combinations and Bliss coefficients were measured by pp28-luciferase. All Bliss coefficients were close to 1, suggesting additive effect between the compounds.

TABLE 3

Bliss coefficient for drug combination

| Compound 1 | $EC_{50}$ | Compound 2 | $EC_{50}$ (μM) | Bliss Coefficient |
|---|---|---|---|---|
| Letermovir | 1.1 ± 0.07 (nM) | MLS8969 | 0.32 ± 0.03 | 1.2 |
| | | NFU1827 | 0.69 ± 0.07 | 1.2 |
| | | MLS8554 | 0.14 ± 0.02 | 0.97 |
| | | MLS8091 | 0.13 ± 0.05 | 1.3 |
| | | NCGC2955 | 3.19 ± 0.17 | 1.09 |
| GCV | 1.33 ± 0.21 (MM) | MLS8969 | 0.72 ± 0.10 | 0.9 |
| GCV | 1.63 ± 0.19 | NFU1827 | 0.69 ± 0.07 | 1.17 |
| GCV | 1.91 ± 0.59 | MLS8554 | 0.55 ± 0.02 | 1.08 |
| GCV | 1.25 ± 0.56 | MLS8091 | 0.57 ± 0.07 | 1.3 |
| GCV | 0.77 ± 0.08 | NCGC2955 | 1.51 ± 0.03 | 0.9 |

Example 9

Discussion and Conclusion. We report the results of the largest HTS to date for HCMV inhibitors using our pp28-luciferase HCMV. This reporter virus has shown high sensitivity and reproducibility for such screening[20]. Its advantage is that HCMV-encoded pp28 is a true late gene, thus its activation represents a near complete cycle of HCMV replication.

Screening campaigns can result in false positive hits and require intense validation. Our combined approach using multiple HCMV strains and several detailed anti-viral assays resulted in the identification and characterization of five distinct hits, each with its unique characteristics. Of the five hits MLS8969 inhibited HCMV entry, MLS8554 and NFU1827 inhibited an immediate early to early stage of HCMV replication (but were different from one another in their effects on other herpesviruses), MLS8091 and NCGC2955 were active at an early-late stage, but NCGC2955 did not have strong suppression of viral DNA replication. All five compounds demonstrated additive effects or mild synergy when combined with GCV or letermovir. No antagonism was found in any of the drug combination experiments. In addition, the five compounds were active against GCV-resistant HCMV, indicating a mechanism separate from the viral DNA polymerase. Future studies should provide insights into the mechanism of action of each of the five compounds. Based on the data presented here, we expect each compound to have a unique mechanism for HCMV suppression.

Screens with libraries containing a limited number of small molecules, different HCMV strains, cell types and timing of treatment have been performed. Three recombinant HCMVs carrying the enhanced yellow fluorescent protein (EYFP) fused with the viral proteins immediate early 2 (IE-2), ppUL32 (pp150), and ppUL83 (pp65) were applied on a cellular kinase library (of 80 compounds) as a pilot screen based on fluorescence intensity and several kinase inhibitors blocked HCMV replication[25]. This screen used a fixed drug concentration of 10 μM at the time of infection and a limited number of hits had no apparent cell toxicity. Reporter cell lines have been generated to screen for anti-HCMV compounds[26, 27]. In one approach using a luciferase reporter cell line, the promoter was activated by IE proteins; therefore, compounds that inhibited HCMV at later stages of infection could not be evaluated[27]. The Gray Kinase Inhibitor library of 187 compounds was successfully screened with HCMV strain AD169, and cells were stained with antibodies to detect the HCMV antigen pp28. Three kinase inhibitors were identified as inhibitors of IE2 production[28]. Recent drug repurposing screening used the Spectrum Collection of 2560 compounds from Micro Discovery System, Inc[29, 30]. Mercorelli used a mechanism-based screening, designed to identify compounds that interfere with the transactivating activity of IE2. Phenotypic assays measured the expression of EGFP fused to IE2[31] or UL99[32]. A major success of HTS was the identification of letermovir (AIC246) from a screen of a compound library[33], which in subsequent studies was shown to have a novel mechanism of action for HCMV inhibition[34].

In conclusion, our study provides several novel compounds that inhibit HCMV replication at sub to low μM concentrations. Each of these compounds represents a good candidate for future mechanistic studies and drug development.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure herein (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure herein and does not pose a limitation on the scope of the disclosure herein unless otherwise claimed. No language in the specification should be construed as indicating any non-claimed element as essential to the practice of the disclosure herein.

The disclosure herein includes all modifications and equivalents of the subject matter recited in the claims appended hereto as permitted by applicable law. Moreover, any combination of the above-described elements in all possible variations thereof is encompassed by the disclosure herein unless otherwise indicated herein or otherwise clearly contradicted by context.

REFERENCE LIST

1. Staras, S. A.; Dollard, S. C.; Radford, K. W.; Flanders, W. D.; Pass, R. F.; Cannon, M. J. Seroprevalence of cytomegalovirus infection in the United States, 1988-1994. *Clin. Infect. Dis* 2006, 43, 1143-1151.
2. Griffiths, P. D.; Clark, D. A.; Emery, V. C. Betaherpesviruses in transplant recipients. *J. Antimicrob. Chemother* 2000, 45 Suppl T3, 29-34.
3. Kovacs, A.; Schluchter, M.; Easley, K.; Demmler, G.; Shearer, W.; La, R. P.; Pitt, J.; Cooper, E.; Goldfarb, J.; Hodes, D.; Kattan, M.; McIntosh, K. Cytomegalovirus infection and HIV-1 disease progression in infants born to HIV-1-infected women. Pediatric Pulmonary and Cardiovascular Complications of Vertically Transmitted HIV Infection Study Group. *N. Engl. J. Med* 1999, 341, 77-84.
4. Sabin, C. A.; Phillips, A. N.; Lee, C. A.; Janossy, G.; Emery, V.; Griffiths, P. D. The effect of CMV infection on progression of human immunodeficiency virus disease is a cohort of haemophilic men followed for up to 13 years from seroconversion. *Epidemiol Infect* 1995, 114, 361-72.
5. Sabin, C. A.; Devereux, H. L.; Clewley, G.; Emery, V. C.; Phillips, A. N.; Loveday, C.; Lee, C. A.; Griffiths, P. D. Cytomegalovirus seropositivity and human immunodeficiency virus type 1 RNA levels in individuals with hemophilia. *J Infect Dis* 2000, 181, 1800-3.
6. Demmler, G. J. Infectious Diseases Society of America and Centers for Disease Control. Summary of a workshop on surveillance for congenital cytomegalovirus disease. *Rev. Infect. Dis* 1991, 13, 315-329.
7. Boeckh, M.; Nichols, W. G.; Papanicolaou, G.; Rubin, R.; Wingard, J. R.; Zaia, J. Cytomegalovirus in hematopoietic stem cell transplant recipients: Current status, known challenges, and future strategies. Biol. *Blood Marrow Transplant* 2003, 9, 543-558.
8. Boivin, G.; Goyette, N.; Rollag, H.; Jardine, A. G.; Pescovitz, M. D.; Asberg, A.; Ives, J.; Hartmann, A.; Humar, A. Cytomegalovirus resistance in solid organ transplant recipients treated with intravenous ganciclovir or oral valganciclovir. *Antivir. Ther* 2009, 14, 697-704.
9. Kimberlin, D. W.; Lin, C. Y.; Sanchez, P. J.; Demmler, G. J.; Dankner, W.; Shelton, M.; Jacobs, R. F.; Vaudry, W.; Pass, R. F.; Kiell, J. M.; Soong, S. J.; Whitley, R. J. Effect of ganciclovir therapy on hearing in symptomatic congenital cytomegalovirus disease involving the central nervous system: a randomized, controlled trial. *J. Pediatr* 2003, 143, 16-25.
10. Schreiber, A.; Harter, G.; Schubert, A.; Bunjes, D.; Mertens, T.; Michel, D. Antiviral treatment of cytomegalovirus infection and resistant strains. *Expert. Opin. Pharmacother* 2009, 10, 191-209.
11. Steininger, C. Novel therapies for cytomegalovirus disease. *Recent Pat Antiinfect. Drug Discov* 2007, 2, 53-72.
12. Chou, S. W. Cytomegalovirus drug resistance and clinical implications. *Transpl. Infect. Dis* 2001, 3 Suppl 2, 20-24.
13. Avery, R. K.; Arav-Boger, R.; Marr, K. A.; Kraus, E.; Shoham, S.; Lees, L.; Trollinger, B.; Shah, P.; Ambinder, R.; Neofytos, D.; Ostrander, D.; Forman, M.; Valsamakis, A. Outcomes in Transplant Recipients Treated with Foscarnet for Ganciclovir-Resistant or Refractory Cytomegalovirus Infection. *Transplantation* 2016.
14. Kimberlin, D. W.; Jester, P. M.; Sanchez, P. J.; Ahmed, A.; Arav-Boger, R.; Michaels, M. G.; Ashouri, N.; Englund, J. A.; Estrada, B.; Jacobs, R. F.; Romero, J. R.; Sood, S. K.; Whitworth, M. S.; Abzug, M. J.; Caserta, M. T.; Fowler, S.; Lujan-Zilbermann, J.; Storch, G. A.; DeBiasi, R. L.; Han, J. Y.; Palmer, A.; Weiner, L. B.; Bocchini, J. A.; Dennehy, P. H.; Finn, A.; Griffiths, P. D.; Luck, S.; Gutierrez, K.; Halasa, N.; Homans, J.; Shane, A. L.; Sharland, M.; Simonsen, K.; Vanchiere, J. A.; Woods, C. R.; Sabo, D. L.; Aban, I.; Kuo, H.; James, S. H.; Prichard, M. N.; Griffin, J.; Giles, D.; Acosta, E. P.; Whitley, R. J. Valganciclovir for symptomatic congenital cytomegalovirus disease. *N. Engl. J. Med* 2015, 372, 933-943.
15. Chou, S.; Ercolani, R. J.; Lanier, E. R. Novel Cytomegalovirus UL54 DNA Polymerase Gene Mutations Selected In Vitro That Confer Brincidofovir Resistance. *Antimicrob Agents Chemother* 2016, 60, 3845-8.
16. Chou, S. Rapid In Vitro Evolution of Human Cytomegalovirus UL56 Mutations That Confer Letermovir Resistance. *Antimicrob Agents Chemother* 2015, 59, 6588-93.
17. Chemaly, R. F.; Ullmann, A. J.; Stoelben, S.; Richard, M. P.; Bornhauser, M.; Groth, C.; Einsele, H.; Silverman, M.; Mullane, K. M.; Brown, J.; Nowak, H.; Kolling, K.; Stobernack, H. P.; Lischka, P.; Zimmermann, H.; Rubsamen-Schaeff, H.; Champlin, R. E.; Ehninger, G. Letermovir for cytomegalovirus prophylaxis in hematopoietic-cell transplantation. *N. Engl. J. Med* 2014, 370, 1781-1789.
18. Frietsch, J. J.; Michel, D.; Stamminger, T.; Hunstig, F.; Birndt, S.; Schnetzke, U.; Scholl, S.; Hochhaus, A.; Hilgendorf, I. In Vivo Emergence of UL56 $C_{325}$Y Cytomegalovirus Resistance to Letermovir in a Patient with Acute Myeloid Leukemia after Hematopoietic Cell Transplantation. *Mediterr J Hematol Infect Dis* 2019, 11, e2019001.
19. Papanicolaou, G. A.; Silveira, F. P.; Langston, A. A.; Pereira, M. R.; Avery, R. K.; Uknis, M.; Wijatyk, A.; Wu, J.; Boeckh, M.; Marty, F. M.; Villano, S. Maribavir for Refractory or Resistant Cytomegalovirus Infections in Hematopoietic-cell or Solid-organ Transplant Recipients: A Randomized, Dose-ranging, Double-blind, Phase 2 Study. *Clin Infect Dis* 2018, 68, 1255-1264.
20. He, R.; Sandford, G.; Hayward, G. S.; Burns, W. H.; Posner, G. H.; Forman, M.; Arav-Boger, R. Recombinant luciferase-expressing human cytomegalovirus (CMV) for evaluation of CMV inhibitors. *Virol. J* 2011, 8, 40.
21. Inglese, J.; Auld, D. S.; Jadhav, A.; Johnson, R. L.; Simeonov, A.; Yasgar, A.; Zheng, W.; Austin, C. P. Quantitative high-throughput screening: a titration-based approach that efficiently identifies biological activities in large chemical libraries. *Proc Natl Acad Sci USA* 2006, 103, 11473-8.
22. Shen, L.; Peterson, S.; Sedaghat, A. R.; McMahon, M. A.; Callender, M.; Zhang, H.; Zhou, Y.; Pitt, E.; Anderson, K. S.; Acosta, E. P.; Siliciano, R. F. Dose-response curve slope sets class-specific limits on inhibitory potential of anti-HIV drugs. *Nat. Med* 2008, 14, 762-766.
23. Sampah, M. E.; Shen, L.; Jilek, B. L.; Siliciano, R. F. Dose-response curve slope is a missing dimension in the analysis of HIV-1 drug resistance. *Proc. Natl. Acad. Sci. U. S. A* 2011, 108, 7613-7618.
24. Jacobson, J. G.; Renau, T. E.; Nassiri, M. R.; Sweier, D. G.; Breitenbach, J. M.; Townsend, L. B.; Drach, J. C. Nonnucleoside pyrrolopyrimidines with a unique mechanism of action against human cytomegalovirus. Antimicrob. *Agents Chemother* 1999, 43, 1888-1894.

25. Straschewski, S.; Warmer, M.; Frascaroli, G.; Hohenberg, H.; Mertens, T.; Winkler, M. Human cytomegaloviruses expressing yellow fluorescent fusion proteins—characterization and use in antiviral screening. *PLoS. One* 2010, 5, e9174.
26. Gilbert, C.; Boivin, G. New reporter cell line to evaluate the sequential emergence of multiple human cytomegalovirus mutations during in vitro drug exposure. *Antimicrob. Agents Chemother* 2005, 49, 4860-4866.
27. Fukui, Y.; Shindoh, K.; Yamamoto, Y.; Koyano, S.; Kosugi, I.; Yamaguchi, T.; Kurane, I.; Inoue, N. Establishment of a cell-based assay for screening of compounds inhibiting very early events in the cytomegalovirus replication cycle and characterization of a compound identified using the assay. *Antimicrob. Agents Chemother* 2008, 52, 2420-2427.
28. Beelontally, R.; Wilkie, G. S.; Lau, B.; Goodmaker, C. J.; Ho, C. M.; Swanson, C. M.; Deng, X.; Wang, J.; Gray, N. S.; Davison, A. J.; Strang, B. L. Identification of compounds with anti-human cytomegalovirus activity that inhibit production of IE2 proteins. *Antiviral Res* 2017, 138, 61-67.
29. Mercorelli, B.; Palu, G.; Loregian, A. Drug Repurposing for Viral Infectious Diseases: How Far Are We? *Trends Microbiol* 2018, 26, 865-876.
30. Mercorelli, B.; Luganini, A.; Nannetti, G.; Tabarrini, O.; Palu, G.; Gribaudo, G.; Loregian, A. Drug Repurposing Approach Identifies Inhibitors of the Prototypic Viral Transcription Factor IE2 that Block Human Cytomegalovirus Replication. *Cell Chem Biol* 2016, 23, 340-51.
31. Gardner, T. J.; Cohen, T.; Redmann, V.; Lau, Z.; Felsenfeld, D.; Tortorella, D. Development of a high-content screen for the identification of inhibitors directed against the early steps of the cytomegalovirus infectious cycle. *Antiviral Res* 2015, 113, 49-61.
32. Nukui, M.; O'Connor, C. M.; Murphy, E. A. The Natural Flavonoid Compound Deguelin Inhibits HCMV Lytic Replication within Fibroblasts. *Viruses* 2018, 10, 614.
33. Lischka, P.; Hewlett, G.; Wunberg, T.; Baumeister, J.; Paulsen, D.; Goldner, T.; Ruebsamen-Schaeff, H.; Zimmermann, H. In vitro and in vivo activities of the novel anticytomegalovirus compound AIC246. *Antimicrob. Agents Chemother* 2010, 54, 1290-1297.
34. Goldner, T.; Hewlett, G.; Ettischer, N.; Ruebsamen-Schaeff, H.; Zimmermann, H.; Lischka, P. The novel anticytomegalovirus compound AIC246 (Letermovir) inhibits human cytomegalovirus replication through a specific antiviral mechanism that involves the viral terminase. *J Virol* 2011, 85, 10884-93.
35. Perez, M.; Lamothe, M.; Maraval, C.; Mirabel, E.; Loubat, C.; Planty, B.; Horn, C.; Michaux, J.; Marrot, S.; Letienne, R.; Pignier, C.; Bocquet, A.; Nadal-Wollbold, F.; Cussac, D.; de Vries, L.; Le Grand, B. Discovery of novel protease activated receptors 1 antagonists with potent antithrombotic activity in vivo. *J Med Chem* 2009, 52, 5826-36.
36. Srinivasan, S.; Schuster, G. B. A conjoined thienopyrrole oligomer formed by using DNA as a molecular guide. *Org Lett* 2008, 10, 3657-60.
37. Kapoor, A.; Cai, H.; Forman, M.; He, R.; Shamay, M.; Arav-Boger, R. Human cytomegalovirus inhibition by cardiac glycosides: evidence for involvement of the HERG gene. *Antimicrob. Agents Chemother* 2012, 56, 4891-4899.
38. Li, R.; Zhu, J.; Xie, Z.; Liao, G.; Liu, J.; Chen, M. R.; Hu, S.; Woodard, C.; Lin, J.; Taverna, S. D.; Desai, P.; Ambinder, R. F.; Hayward, G. S.; Qian, J.; Zhu, H.; Hayward, S. D. Conserved Herpesvirus Kinases Target the DNA Damage Response Pathway and TIP60 Histone Acetyltransferase to Promote Virus Replication. *Cell Host. Microbe* 2011, 10, 390-400.
39. Forman, M. S.; Vaidya, D.; Bolorunduro, O.; Diener-West, M.; Pass, R. F.; Arav-Boger, R. Cytomegalovirus Kinetics Following Primary Infection in Healthy Women. *J Infect Dis* 2017, 215, 1523-1526.
40. Cai, H.; Kapoor, A.; He, R.; Venkatadri, R.; Forman, M.; Posner, G. H.; Arav-Boger, R. In Vitro Combination of Anti-Cytomegalovirus Compounds Acting through Different Targets: Role of the Slope Parameter and Insights into Mechanisms of Action. *Antimicrob. Agents Chemother* 2014, 58, 986-994.
41. Jilek, B. L.; Zarr, M.; Sampah, M. E.; Rabi, S. A.; Bullen, C. K.; Lai, J.; Shen, L.; Siliciano, R. F. A quantitative basis for antiretroviral therapy for HIV-1 infection. *Nat. Med* 2012, 18, 446-451.

What is claimed is:

1. A method of inhibiting a human herpesvirus in a subject in need thereof, comprising administering to the subject a compound of formula I or a pharmaceutical composition thereof comprising a pharmaceutically acceptable carrier, wherein formula I is:

(I)

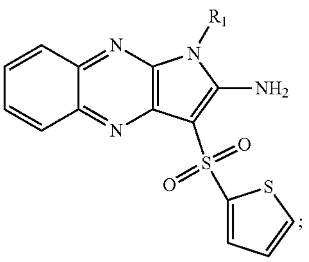

or a salt, solvate, or stereoisomer thereof, wherein $R_1$ is a cycloalkyl, heterocycloalkyl, aryl, or heteroaryl optionally substituted with one or more amidinyl, guanidinyl, phosphate, sulfate, tetrazole, 3-hydroxyisoxazole, secondary amides, sulfonamides, sulfonyl ureas, acylamidines, acylguanidines, having 1 to 10 carbon atoms and linked via a $C_1$-$C_3$ alky group.

2. The method of claim 1, wherein the compound is formula I and selected from the group consisting of:

(A)

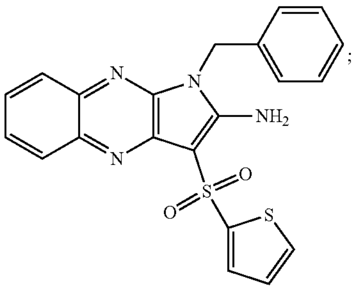

-continued (B)

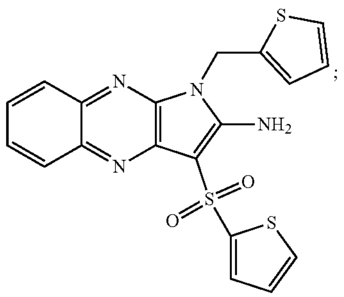

and (C)

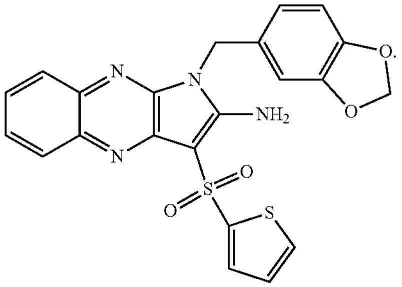

3. The method of claim 1, wherein the herpesvirus is selected from the group consisting of human herpesvirus 1 (HHV-1), human herpesvirus 2 (HHV-2), human herpesvirus 3 (HHV-3), human herpesvirus 4 (HHV-4), human herpesvirus 5 (HHV-5), human herpesvirus 61 (HHV-6), human herpesvirus 7 (HHV-7), and human herpesvirus 8 (HHV-8).

4. The method of claim 3, wherein the herpesvirus is HHV-5, and further wherein the HHV-5 is ganciclovir resistant.

5. The method of claim 1, further comprising administering more than one biologically active agent.

6. The method of claim 1, further comprising administering ganciclovir or letermovir.

* * * * *